United States Patent
Minagawa et al.

(10) Patent No.: US 10,760,084 B2
(45) Date of Patent: Sep. 1, 2020

(54) α-AMYLASE-BINDING NUCLEIC ACID MOLECULE AND USE THEREOF

(71) Applicants: NEC Solution Innovators, Ltd., Tokyo (JP); Gunma University, Gunma (JP)

(72) Inventors: Hirotaka Minagawa, Tokyo (JP); Katsunori Horii, Tokyo (JP); Jou Akitomi, Tokyo (JP); Naoto Kaneko, Tokyo (JP); Ikuo Shiratori, Tokyo (JP); Iwao Waga, Tokyo (JP); Masayasu Kuwahara, Gunma (JP)

(73) Assignees: NEC Solution Innovators, Ltd., Tokyo (JP); Gunma University, Gunma (JP)

( * ) Notice: Subject to any disclaimer, the term of this patent is extended or adjusted under 35 U.S.C. 154(b) by 212 days.

(21) Appl. No.: 15/775,797

(22) PCT Filed: Sep. 12, 2016

(86) PCT No.: PCT/JP2016/076741
§ 371 (c)(1),
(2) Date: May 11, 2018

(87) PCT Pub. No.: WO2017/081926
PCT Pub. Date: May 18, 2017

(65) Prior Publication Data
US 2018/0327746 A1 Nov. 15, 2018

(30) Foreign Application Priority Data

Nov. 13, 2015 (JP) ................................ 2015-222952

(51) Int. Cl.
| | |
|---|---|
| *C12N 15/11* | (2006.01) |
| *C12N 15/115* | (2010.01) |
| *C12Q 1/40* | (2006.01) |
| *C12Q 1/68* | (2018.01) |
| *G01N 33/53* | (2006.01) |
| *C12N 15/10* | (2006.01) |

(52) U.S. Cl.
CPC .............. *C12N 15/115* (2013.01); *C12Q 1/40* (2013.01); *C12Q 1/68* (2013.01); *G01N 33/53* (2013.01); *C12N 15/1048* (2013.01); *C12N 2310/16* (2013.01); *C12N 2310/335* (2013.01); *C12Y 302/01001* (2013.01)

(58) Field of Classification Search
None
See application file for complete search history.

(56) References Cited

U.S. PATENT DOCUMENTS

| | | |
|---|---|---|
| 2007/0178476 A1 | 8/2007 | Shima et al. |
| 2016/0298117 A1 | 10/2016 | Murata et al. |

FOREIGN PATENT DOCUMENTS

| | | |
|---|---|---|
| EP | 3078747 A1 | 10/2016 |
| JP | 2008-507284 A | 3/2008 |
| WO | WO-2006012468 A2 | 2/2006 |
| WO | WO-2014142933 A1 | 9/2014 |
| WO | WO-2015083391 A1 | 6/2015 |
| WO | WO-2015151350 A1 | 10/2015 |

OTHER PUBLICATIONS

International Search Report, Corresponding to PCT/JP2016/076741, dated Dec. 6, 2016, 2 pp.
Verity et al., "Development of a Field Enzyme-Linked Immunosorbent Assay (ELISA) for Detection of α-Amylase in Preharvest-Sprouted Wheat," Cereal Chemistry, vol. 76, No. 5, pp. 673-681, (1999), 9 pp.
Higson, "Biosensors for Medical Applications," Woodhead Publishing, pp. i-xviii, 2.4 Piezoelectric Biosensors with Biomimeticreceptors, pp. 53-64, 10.3.3 Detection of Salivary Enzyme Amylase Using an Electrochemical Biosensor, pp. 280-287, (2012), 46 pp.
Nonaka et al., "Afinnity Improvement of a VEGF Aptamer by in Silico Maturation for a Sensitive VEGF-Detection System," Anal., Chem., vol. 85, pp. 1132-1137 (2013), 6 pp.
Matsuda et al., "Thermal Stability and Nuclease-resistance Properties of Oligonucleotides having an Aminoalkyl Side Chain at the Nucleobase and sugar Moieties," Frontiers in Nucleosides and Nucleic Acids, pp. 549-576 (2005), 28 pp.

*Primary Examiner* — Ekaterina Poliakova-Georgantas
(74) *Attorney, Agent, or Firm* — Wilmer Cutler Pickering Hale and Dorr LLP

(57) ABSTRACT

The present invention provides a novel nucleic acid molecule that can be used for detection of α-amylase. The α-amylase-binding nucleic acid molecule of the present invention is characterized in that it binds to α-amylase with a dissociation constant of 17 nM or less, and preferably includes a polynucleotide consisting of any of base sequences of SEQ ID NOs: 1 to 22, for example. According to the nucleic acid molecule of the present invention, it is possible to detect α-amylase in saliva.

12 Claims, 17 Drawing Sheets

Specification includes a Sequence Listing.

SEQ ID NO: 3 : AML1243KR8m3

SEQ ID NO: 4 : AML1243KR8m4

SEQ ID NO: 7 : AML1243KR8m1s65_FW_s20

SEQ ID NO: 8 : AML1243KR8m1s65_FW_s15

SEQ ID NO: 9 : AML1243KR8m1s58_FW_s20

SEQ ID NO: 10 : AML1243KR8m1s58_FW_s15

SEQ ID NO: 11 : AML1243KR8m2s63

SEQ ID NO: 12 : AML1243KR8m2s49

SEQ ID NO: 13 : AML1243KR8m2s49Fw_s20

SEQ ID NO: 14 : AML1243KR8m2s49Fw_s15

SEQ ID NO: 15 : AML1243KR8m3s63

SEQ ID NO: 16 : AML1243KR8m3s63Fw_s20

SEQ ID NO: 17 : AML1243KR8m3s63Fw_s15

SEQ ID NO: 18 : Amy_258KK10R8m1

ABBREVIATED # α-AMYLASE-BINDING NUCLEIC ACID MOLECULE AND USE THEREOF

CROSS-REFERENCE TO RELATED APPLICATIONS

The present application is a national stage application of International Application No. PCT/JP2016/076741 entitled "Nucleic Acid Molecule Binding to α-amylase and use thereof," filed on Sep. 12, 2016, which claims the benefit of priority from Japanese Patent Application No. 2015-222952, filed on Nov. 13, 2015, the disclosures of which are incorporated herein in their entirety by reference thereto.

TECHNICAL FIELD

The present invention relates to a nucleic acid molecule that binds to α-amylase and use thereof.

SEQUENCE LISTING

The instant application contains a Sequence Listing which has been submitted electronically in ASCII format and is hereby incorporated by reference in its entirety. Said ASCII copy, created on Jun. 27, 2016, is named TF15019WO_ST25.txt and is 6,229 bytes in size.

BACKGROUND ART

From the fact that stress can cause fatigue and depression, great importance is placed on stress check in recent years. However, there is a problem in that it is difficult to check whether a person is under stress by other persons owing to the fact that the person himself/herself may not be aware of the stress or that the stress is a subjective matter, for example. Under these circumstances, there is a demand for the establishment of a method for checking stress objectively.

It is known that, when humans feel stress, secretion of α-amylase in saliva increases. On this account, there has been an attempt to evaluate stress indirectly by measuring α-amylase in the saliva. Specifically, an ELISA method using an antibody against α-amylase as an antigen has been reported (Non-Patent Document 1).

However, antibodies are proteins and thus have a problem in stability. Accordingly, it is difficult to use an antibody in a test method that can be carried out easily at low cost.

CITATION LIST

Non-Patent Document(s)

Non-Patent Document 1: J. Christiana K. Verity et al., Development of a Field Enzyme-Linked Immunosorbent Assay (ELISA) for Detection of α-Amylase in Preharvest-Sprouted Wheat, Cereal Chemistry, 1999, Vol. 76, no. 5, pp. 673-681.

BRIEF SUMMARY OF THE INVENTION

Problem to be Solved by the Invention

With the foregoing in mind, it is an object of the present invention is to provide a novel molecule that can be used for detection of α-amylase.

Means for Solving Problem

The present invention provides an α-amylase-binding nucleic acid molecule that binds to α-amylase with a dissociation constant of 17 nM or less.

The present invention also provides an α-amylase analysis sensor including the α-amylase-binding nucleic acid molecule according to the present invention.

The present invention also provides an α-amylase analysis method including the step of: detecting α-amylase in a specimen by causing the specimen and a nucleic acid molecule to come into contact with each other, wherein the nucleic acid molecule is the α-amylase-binding nucleic acid molecule according to the present invention, and in the detection step, the nucleic acid molecule is caused to bind to the α-amylase in the specimen, and the α-amylase in the specimen is detected by detecting the binding.

Effects of the Invention

The α-amylase-binding nucleic acid molecule of the present invention can bind to α-amylase with the above-described dissociation constant. Thus, the α-amylase-binding nucleic acid molecule of the present invention can detect α-amylase in a specimen with high accuracy on the basis of the presence or absence of the binding with the α-amylase, for example. Therefore, it can be said that the α-amylase-binding nucleic acid molecule of the present invention is a very useful tool for the detection of α-amylase in the fields of preventive medicine, health care, pathological diagnosis of diseases such as pancreas cancer and diabetes, diagnosis of stress, and the like, for example.

DESCRIPTION OF EXEMPLARY EMBODIMENTS

Figure 1A:
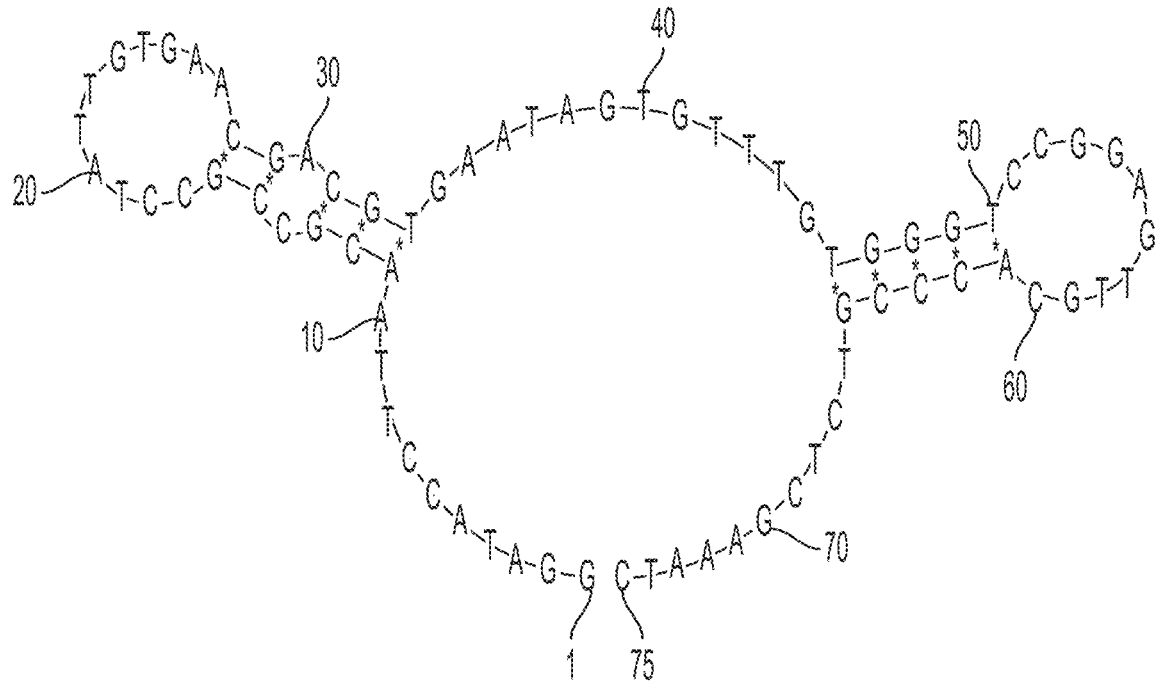
FIG. 1A is a schematic view showing examples of predicted secondary structures of α-amylase-binding nucleic acid molecules of the present invention.
Figure 1A:
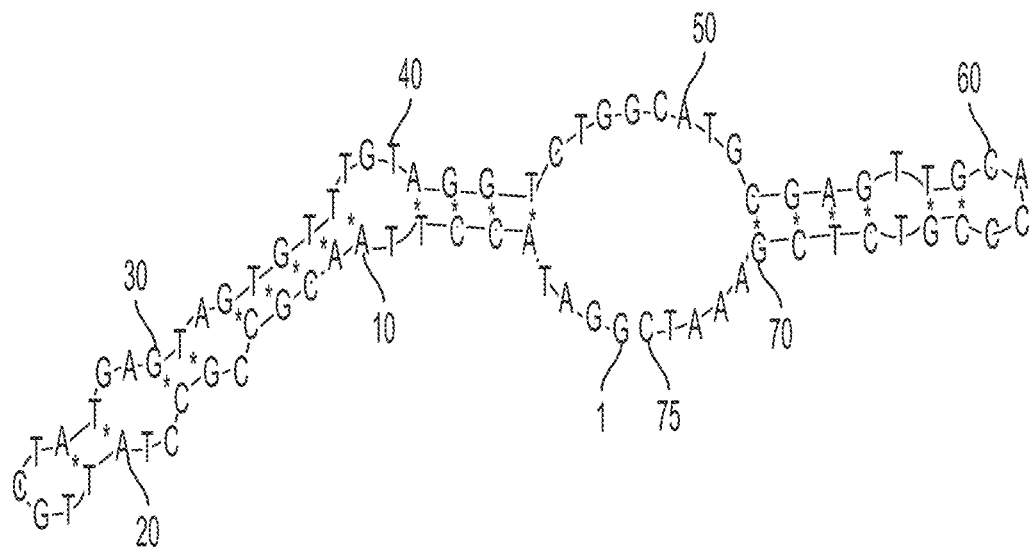
Figure 1A:
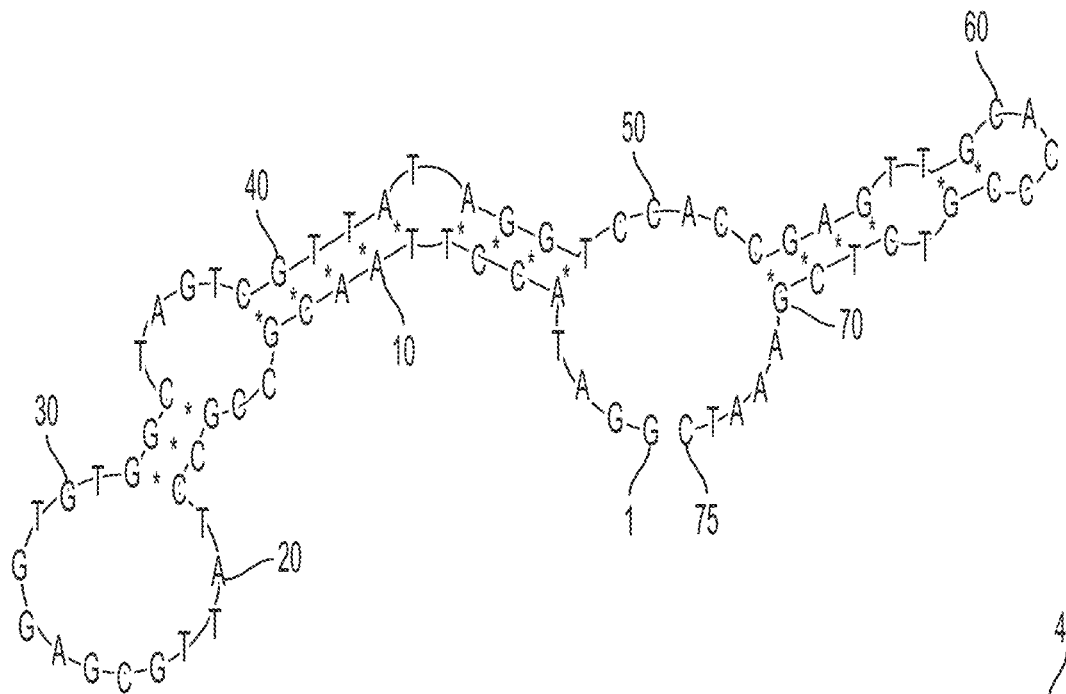
Figure 1:
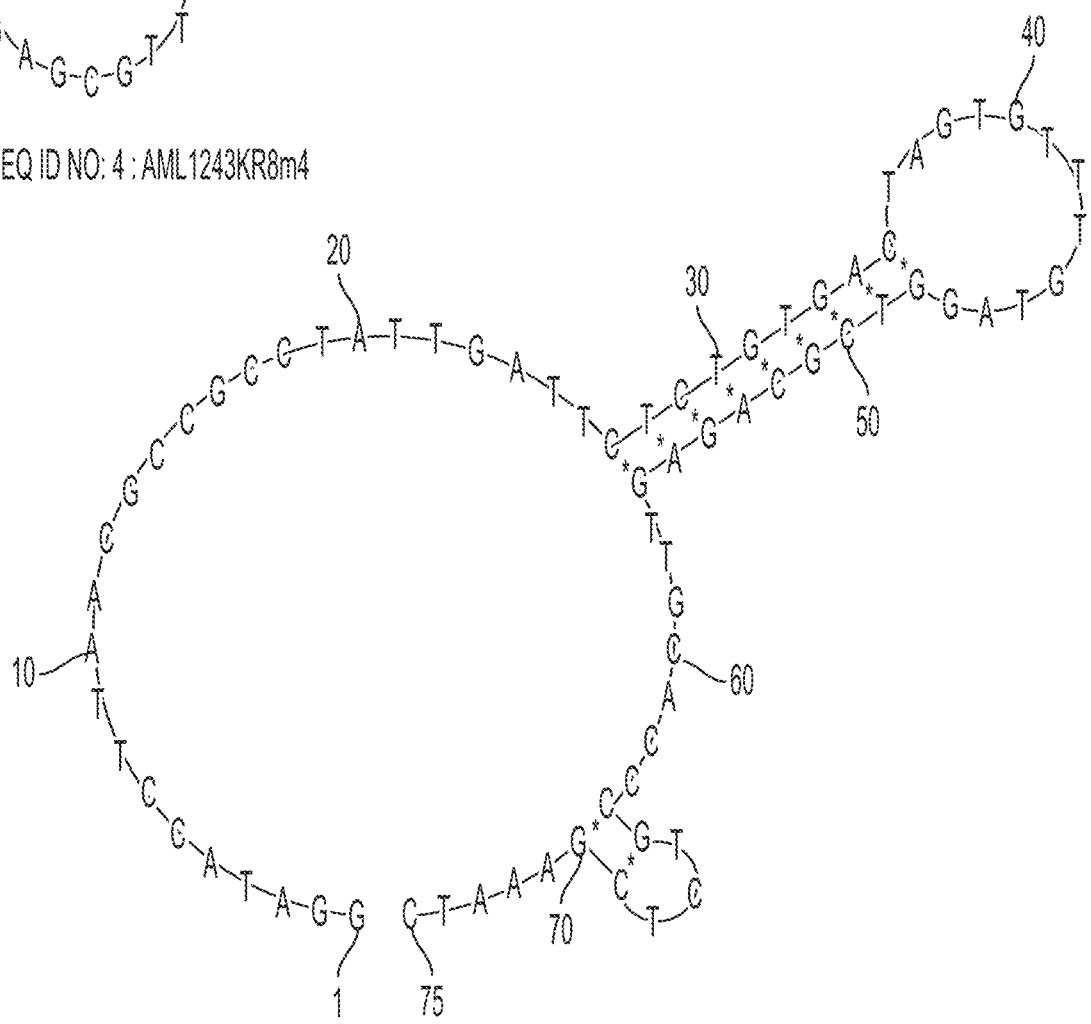
FIG. 1B is a schematic view showing examples of predicted secondary structures of other α-amylase-binding nucleic acid molecules of the present invention.
FIG. 1C is a schematic view showing examples of predicted secondary structures of still other α-amylase-binding nucleic acid molecules of the present invention.
FIG. 1D is a schematic view showing examples of predicted secondary structures of still other α-amylase-binding nucleic acid molecules of the present invention.
FIG. 1E is a schematic view showing examples of predicted secondary structures of still other α-amylase-binding nucleic acid molecules of the present invention.
FIG. 1F is a schematic view showing examples of predicted secondary structures of still other α-amylase-binding nucleic acid molecules of the present invention.
Figure 1B:
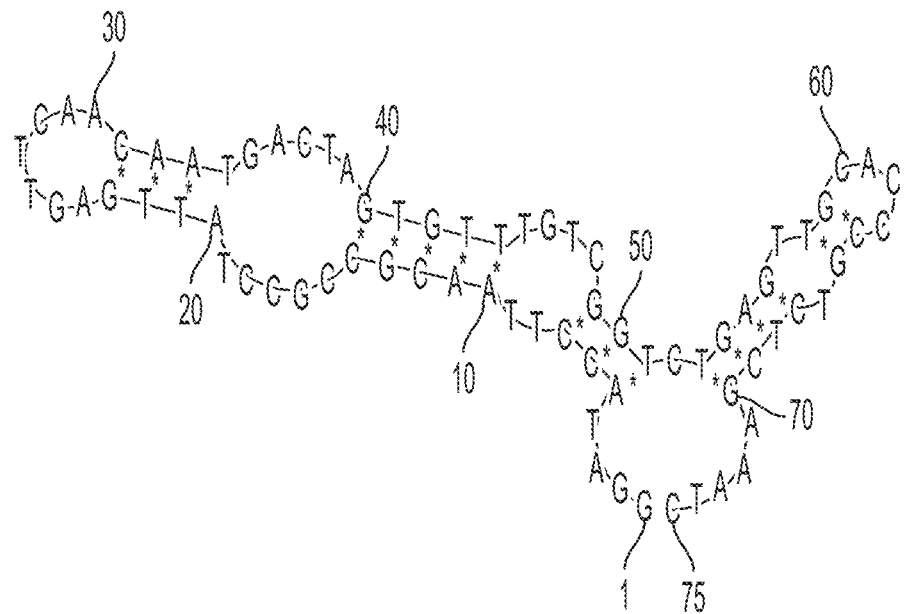
Figure 1B:
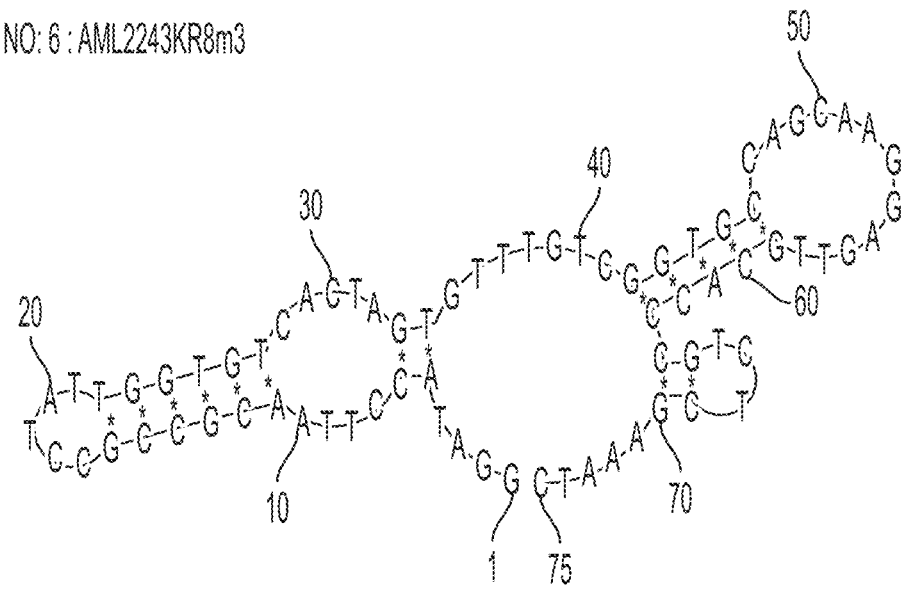
Figure 1B:
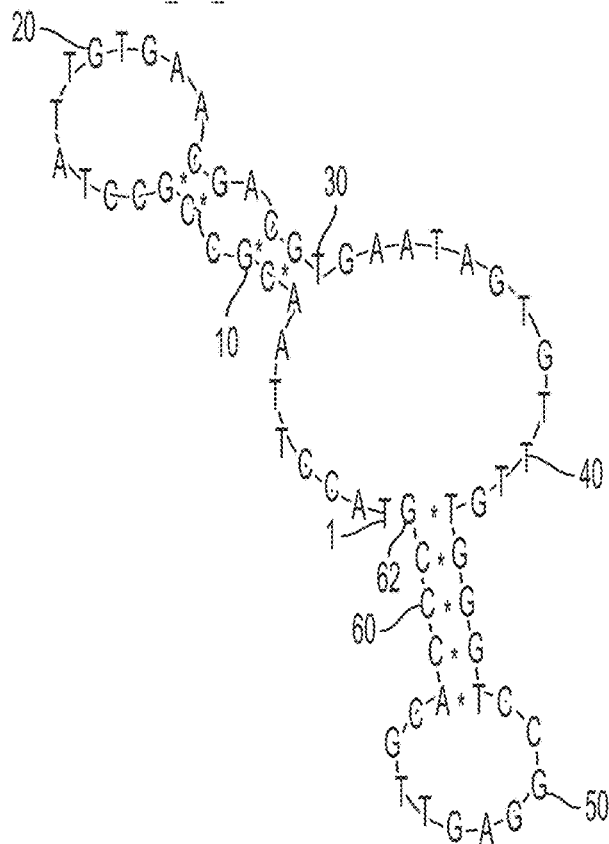
Figure 1:
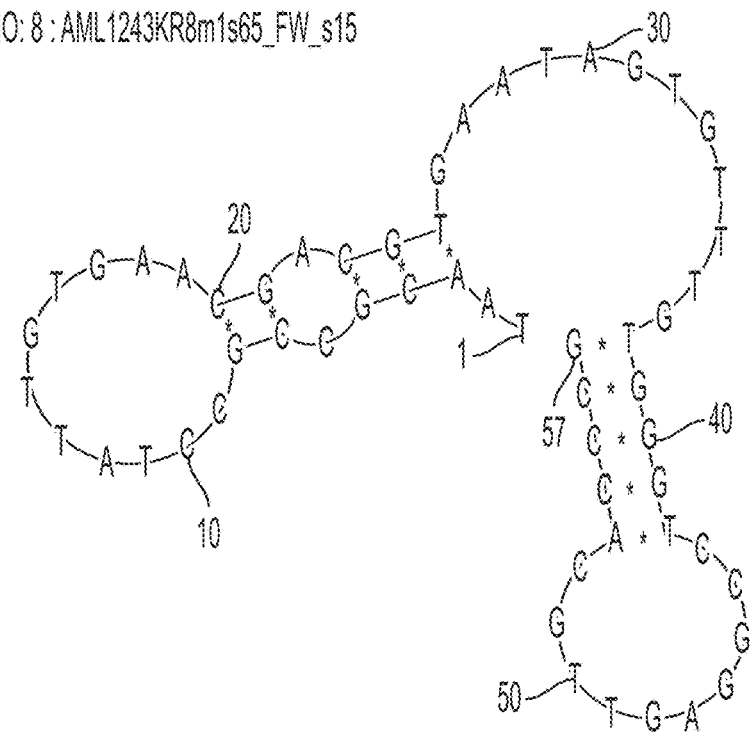
Figure 1C:
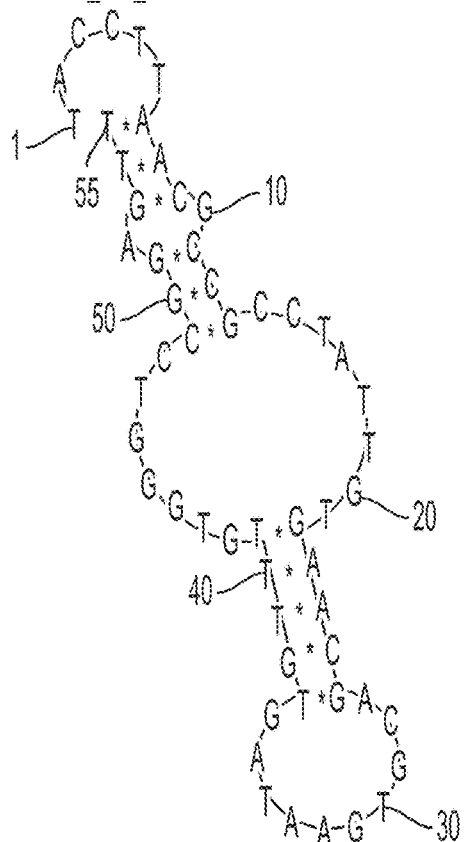
Figure 1C:
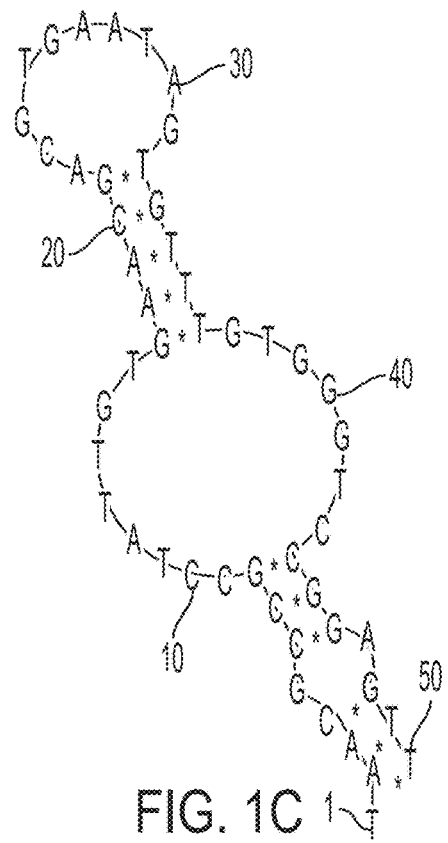
Figure 1C:
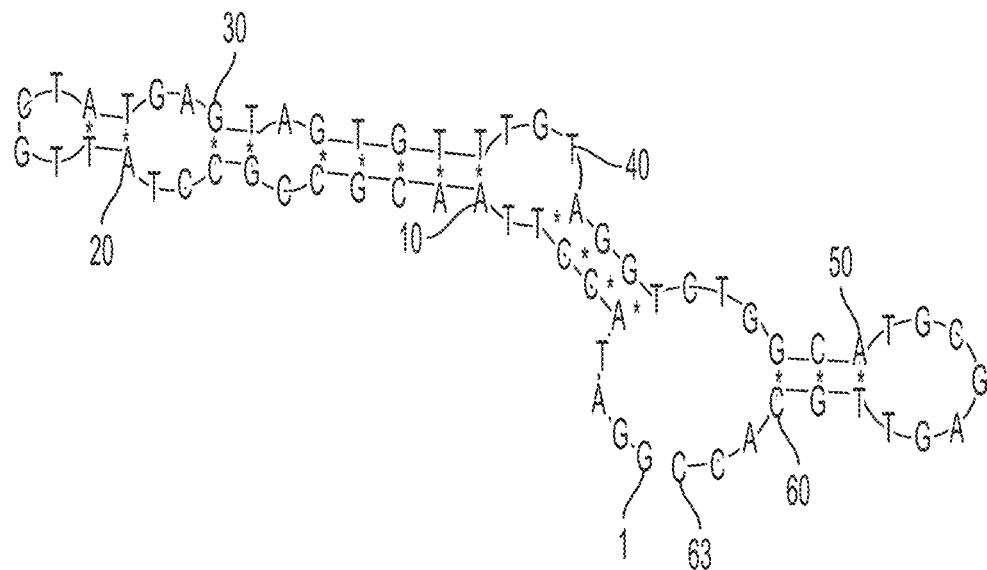
Figure 1:
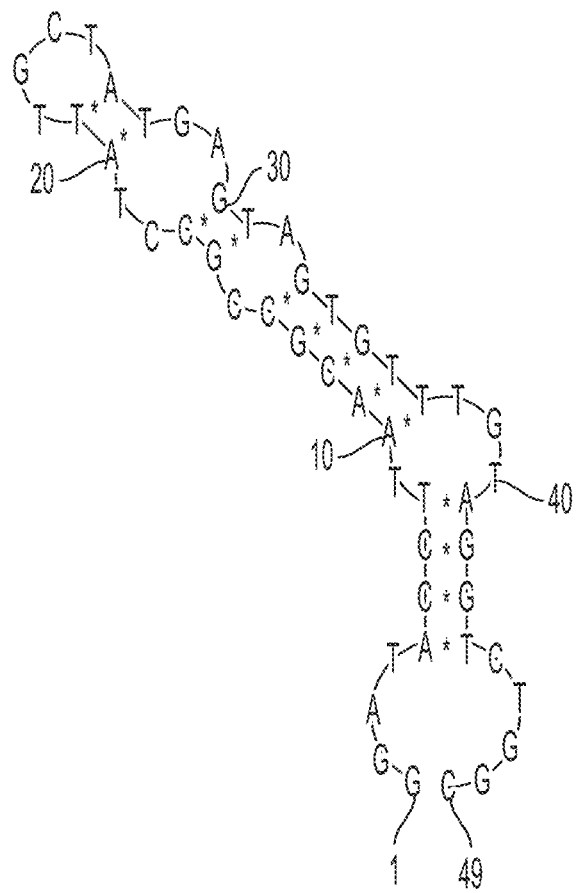
Figure 1D:
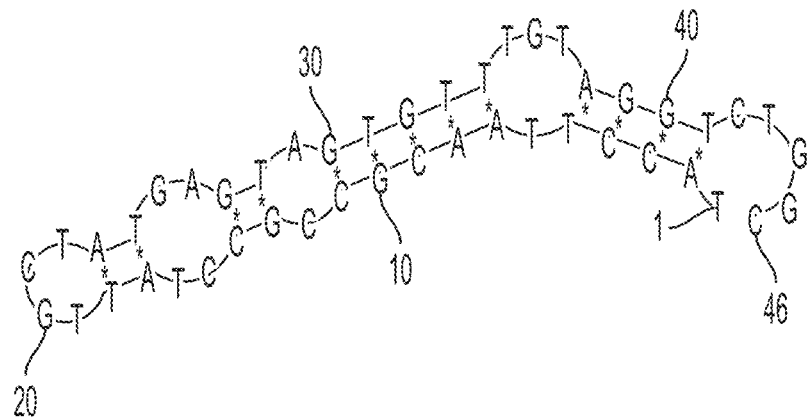
Figure 1D:
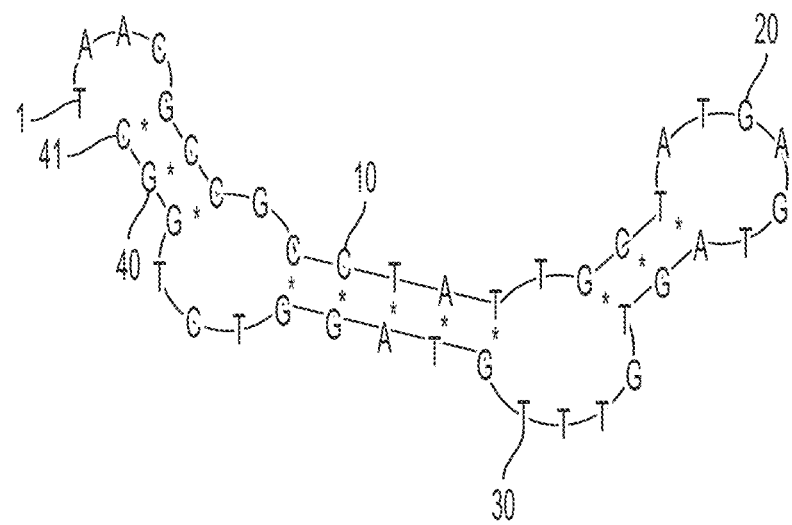
Figure 1D:
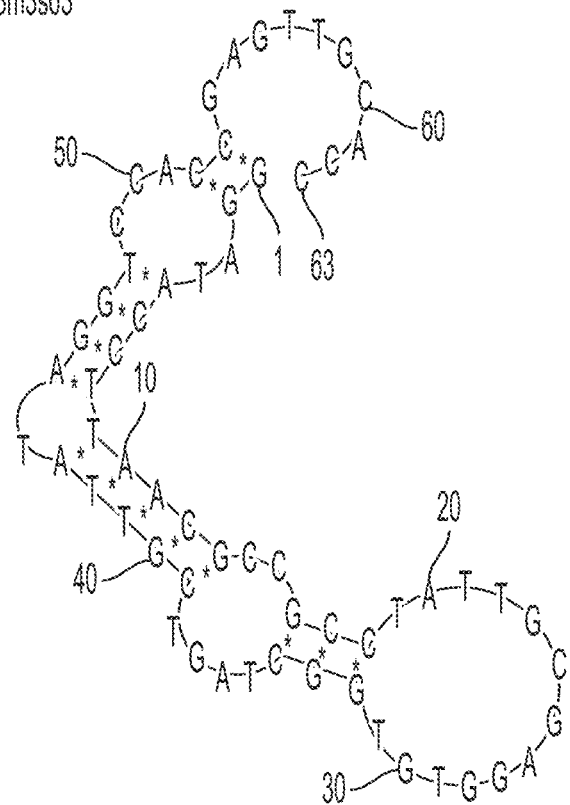
Figure 1:
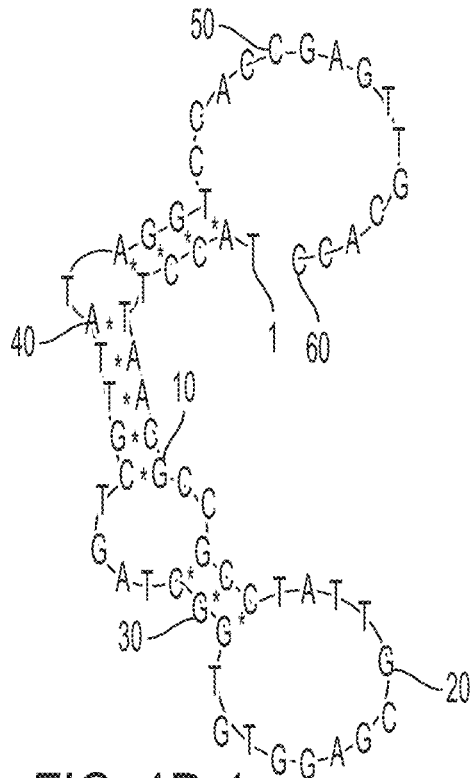
Figure 1E:
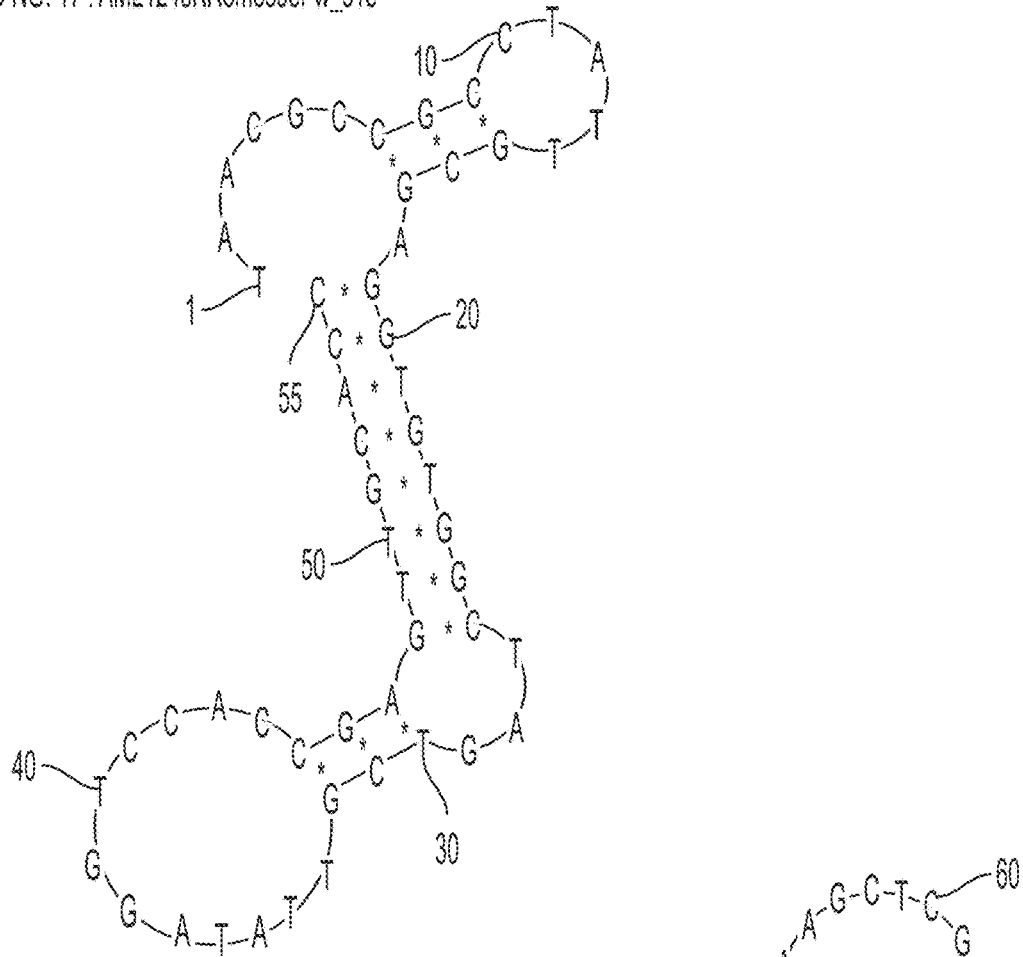
Figure 1E:
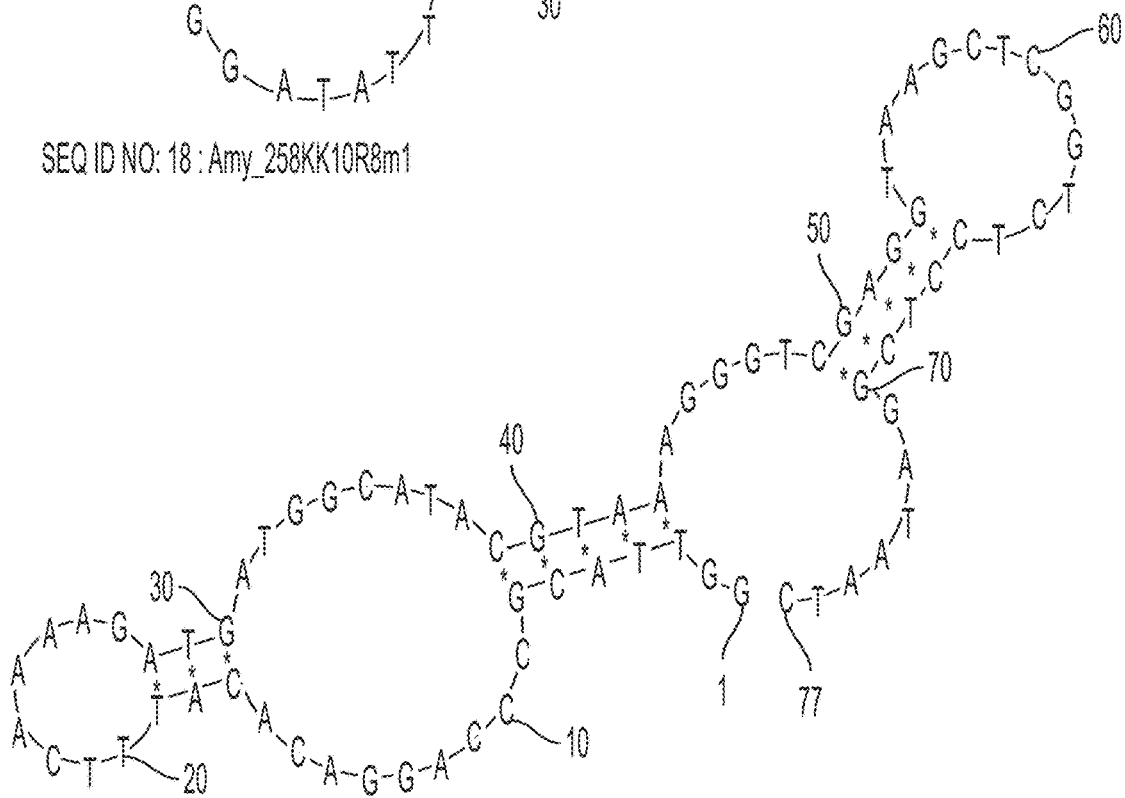
Figure 1E:
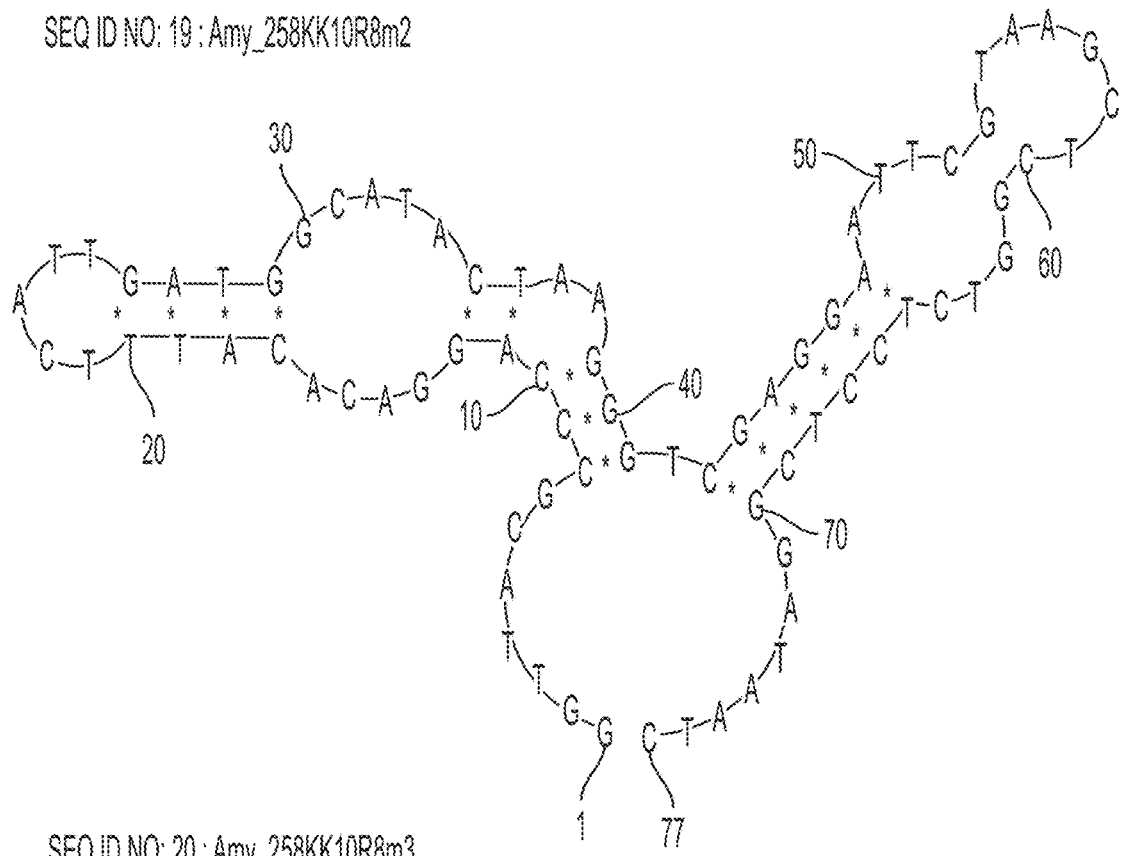
Figure 1:
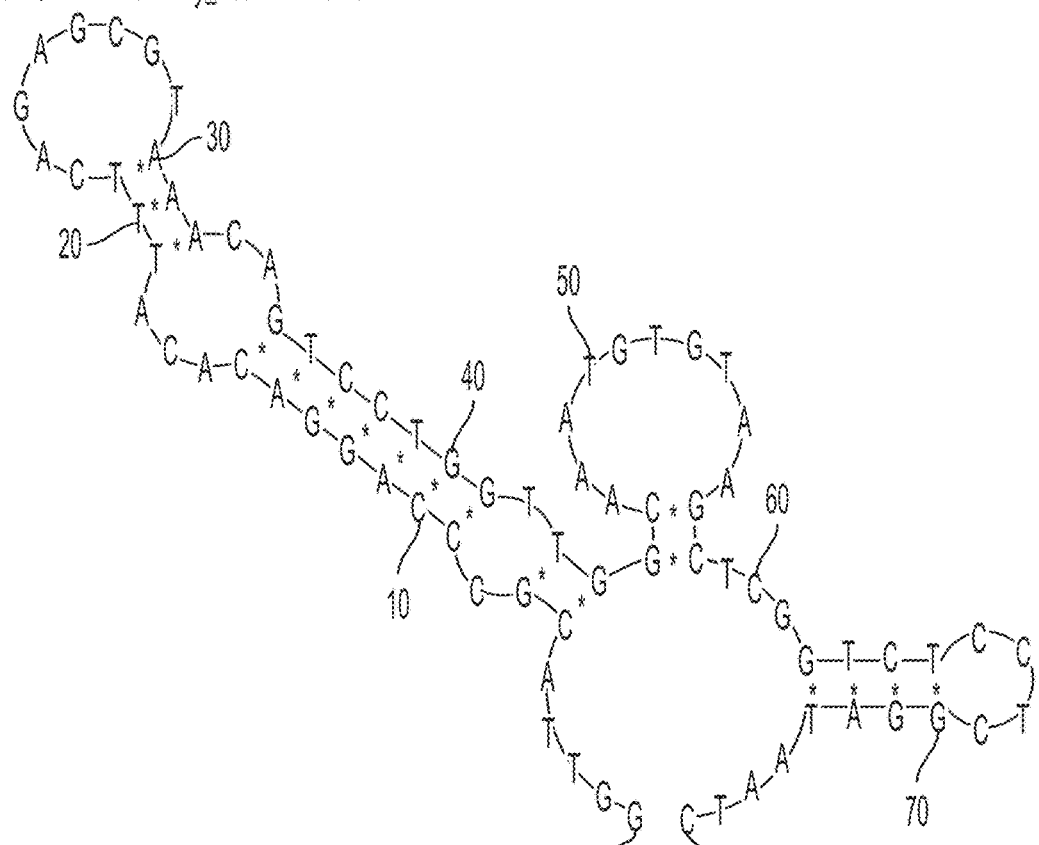
Figure 1F:
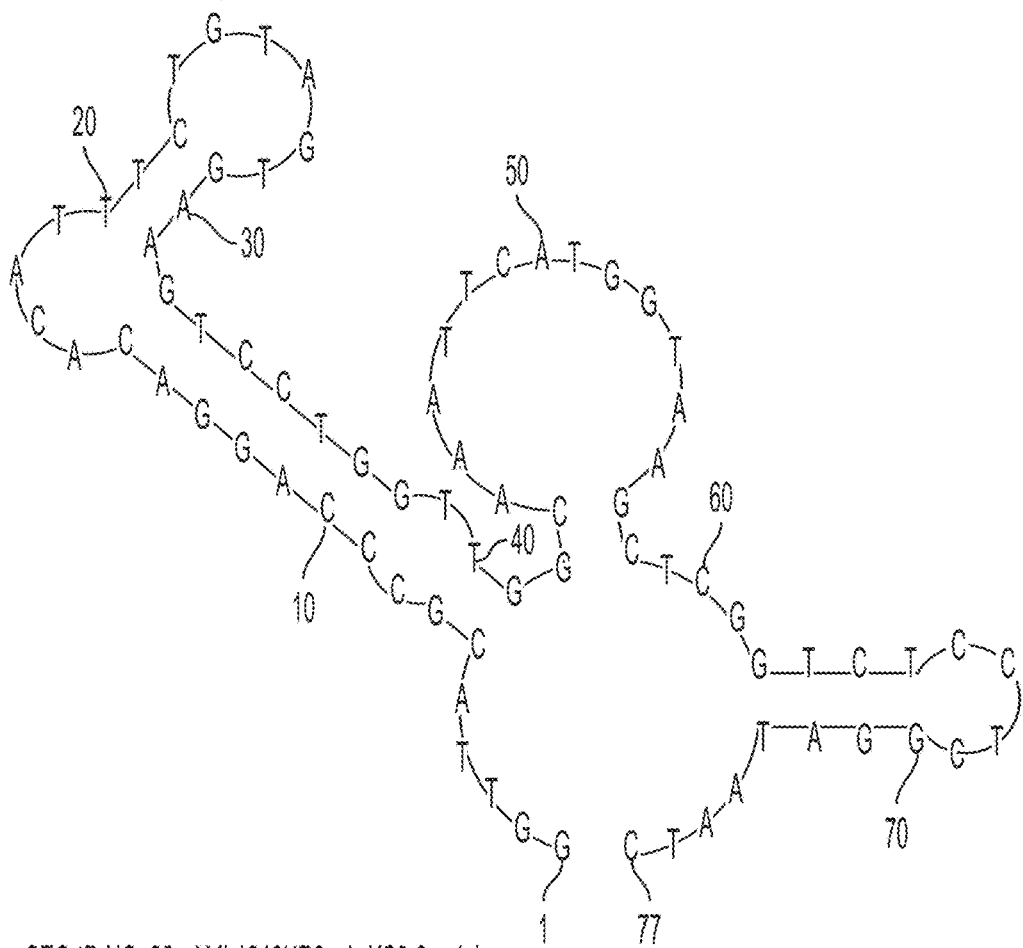
Figure 1F:
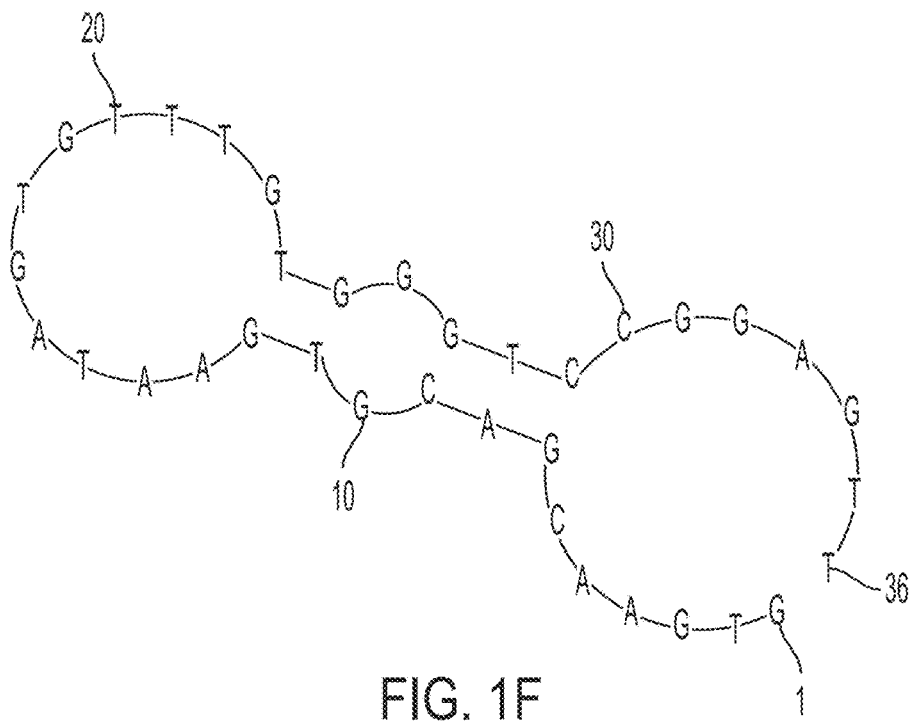

The α-amylase-binding nucleic acid molecule of the present invention may include the following polynucleotide (a), for example. The α-amylase-binding nucleic acid molecule of the present invention also may be referred to as "the nucleic acid molecule of the present invention" hereinafter.
(a) a polynucleotide consisting of any of base sequences of SEQ ID NOs: 1 to 6 and 18 to 21

The α-amylase-binding nucleic acid molecule of the present invention may be, for example, at least one polynucleotide selected from the group consisting of the following polynucleotides (a1), (a2), and (a3).
(a1) a polynucleotide consisting of any of base sequences of SEQ ID NOs: 7 to 10 and 22
(a2) a polynucleotide consisting of any of base sequences of SEQ ID NOs: 11 to 14
(a3) a polynucleotide consisting of any of base sequences of SEQ ID NOs: 15 to 17

The nucleic acid molecule of the present invention may include, for example, a modified base, which is a base modified with a modifying group.

In the nucleic acid molecule of the present invention, the modified base may be a modified thymine, for example.

In the nucleic acid molecule of the present invention, the modifying group may be an adenine residue or a substituted adenine residue, for example.

In the nucleic acid molecule of the present invention, the substituted adenine residue may have a substituent bound to N at a 9-position, for example.

In the nucleic acid molecule of the present invention, the substituent may be an amidino aminoalkyl group, for example.

In the nucleic acid molecule of the present invention, the amidino aminoalkyl group may be a 4-amidino aminobutyl group, for example.

In the nucleic acid molecule of the present invention, the modified base may be a modified purine base with a 7-position of a purine base being modified with the modifying group or a modified pyrimidine base with a 5-position of a pyrimidine base being modified with the modifying group, for example.

In the nucleic acid molecule of the present invention, the polynucleotide may be a DNA, for example.

In the analysis method of the present invention, the specimen may be at least one selected from the group consisting of saliva, urine, plasma, and serum, for example.

The present invention will be described specifically below.

(1) α-amylase-binding nucleic acid molecule

As described above, the α-amylase-binding nucleic acid molecule of the present invention is characterized in that it binds to α-amylase with a dissociation constant of 17 nM or less.

The nucleic acid molecule of the present invention can bind to α-amylase, as described above. The α-amylase is not particularly limited, and the α-amylase may be derived from a human or a non-human animal, for example. Examples of the non-human animal include mice, rats, monkeys, rabbits, dogs, cats, horses, cows, and pigs. Amino acid sequence information on human α-amylase is registered under Accession No. P04745 in UniProt (http://www.uniprot.org/), for example.

In the present invention, the expression "binds to α-amylase" (and grammatical variations thereof) also is referred to as "has binding ability to α-amylase" or "has binding activity to α-amylase", for example. The binding between the nucleic acid molecule of the present invention and the α-amylase can be determined by surface plasmon resonance (SPR) analysis or the like, for example. The analysis can be performed using ProteON (trade name, BioRad), for example. Since the nucleic acid molecule of the present invention binds to α-amylase, it can be used for detection of the α-amylase, for example.

The nucleic acid molecule of the present invention binds to α-amylase with a dissociation constant of 17 nM or less, 5 nM or less, or 1 nM or less, for example. The minimum detectable concentration of the α-amylase by the nucleic acid molecule of the present invention is 20 nM, 10 nM, or 5 nM, for example.

The nucleic acid molecule of the present invention may be a nucleic acid molecule including the following polynucleotide (a), examples of which are shown in Tables 1A and 1B below.
(a) a polynucleotide consisting of any of base sequences of SEQ ID NOs: 1 to 6 and 18 to 21

TABLE 1A

| SEQ ID NO | name | Modified base | Sequence |
|---|---|---|---|
| 1 | AML1243KR8m1 | KS9 | GGATACCTTAACGCCGCCTATTGTGAACGACGTGAATAGTGTTTGTGGGTCCGGAGTTGCACCCGTCTCGAAATC |
| 2 | AML1243KR8m2 | KS9 | CGATACCTTAACGCCGCCTATTGCTATGAGTAGTGTTTGTAGGTCTGGCATGCGAGTTGCACCCGTCTCGAAATC |
| 3 | AML1243KR8m3 | KS9 | GGATACCTTAACGCCGCCTATTGCGAGGTGTGGCTAGTCGTTATAGGTCCACCGAGTTGCACCCGTCTCGAAATC |
| 4 | AML1243KR8m4 | KS9 | GGATACCTTAACGCCGCCTATTGATTCTCTGTGACTAGTGTTTGTAGGTCGCAGAGTTGCACCCGTCTCGAAATC |
| 5 | AML1243KR8m5 | KS9 | GGATACCTTAACGCCGCCTATTGAGTTCAACAATGACTAGTGTTTGTCGGTCTGAGTTGCACCCGTCTCGAAATC |

TABLE 1A-continued

| SEQ ID NO | name | Modified base | Sequence |
|---|---|---|---|
| 6 | AML2243KR8m3 | KS9 | GGATACCTTAACGCCGCCTATTGGTGTCACTAGTGTTTGTCGGTGCCAGCAAGGAGT TGCACCCGTCTCGAAATC |

TABLE 1B

| SEQ ID NO | name | Modified base | Sequence |
|---|---|---|---|
| 18 | Amy_258KK10R8m1 | KK10 | GGTTACGCCCAGGACACATTTCAAAAGATGATGGCATACGTAAAGGGTCGAGG TAAG CTCGGTCTCCTCGGATAATC |
| 19 | Amy_258KK10R8m2 | KK10 | GGTTACGCCCAGGACACATTTCATTGATGGCATACTAAGGGTCGAGGAATTCG TAAG CTCGGTCTCCTCGGATAATC |
| 20 | Amy_258KK10R8m3 | KK10 | GGTTACGCCCAGGACACATTTCAGACCGTAAACAGTCCTGGTTGGCAAATGTG TAAG CTCGGTCTCCTCGGATAATC |
| 21 | Amy_258KK10R8m4 | KK10 | GGTTACGCCCAGGACACATTTCTGTAGTGAAGTCCTGGTTGGCAAATTCATGG TAAG CTCGGTCTCCTCGGATAATC |

The nucleic acid molecule of the present invention may be, for example, a nucleic acid molecule including a polynucleotide consisting of a partial sequence of any of the polynucleotides (a).

The polynucleotide consisting of the partial sequence may be, for example, at least one polynucleotide selected from the group consisting of the following polynucleotides (a1), (a2), and (a3).

(a1) a polynucleotide consisting of any of base sequences of SEQ ID NOs: 7 to 10 and 22

(a2) a polynucleotide consisting of any of base sequences of SEQ ID NOs: 11 to 14

(a3) a polynucleotide consisting of any of base sequences of SEQ ID NOs: 15 to 17

The polynucleotide (a1) defines examples of a partial sequence of SEQ ID NO: 1. The polynucleotide (a2) defines examples of a partial sequence of SEQ ID NO: 2. The polynucleotide (a3) defines examples of a partial sequence of SEQ ID NO: 3. These sequences are shown in Table 2 below.

TABLE 2

| SEQ ID NO | name | Modified base | Sequence |
|---|---|---|---|
| 1 | AML1243KR8m1 | KS9 | GGATACCTTAACGCCGCCTATTGTGAACGACGTGAATAGTGTTTGTGGGTCCGGAGT TGCACCGTTCTCGAAATC |
| 7 | AML1243KR8m1 s65_FW_s20 | KS9 | TACCTTAACGCCGCCTATTGTGAACGACGTGAATAGTGTTTGTGGGTCCGGAGTTGC ACCCG |
| 8 | AML1243KR8m1 s65_FW_s15 | KS9 | TAACGCCGCCTATTGTGAACGACGTGAATAGTGTTTGTGGGTCCGGAGTTGCACCCG |
| 9 | AML1243KR8m1 s5B_FW_s20 | KS9 | TACCTTAAGGCCGCGTATTGTGAACGACGTGAATAGTGTTTGTGGGTCCGGAGTT |
| 10 | AML1243KR8m1 s5B_FW_s15 | KS9 | TAACGCCGCCTATTGTGAACGACGTGAATAGTGTTTGTGGGTCCGGAGTT |
| 22 | AML1243KR8m1_ KS9-3_mini | KS9 | GTGAACGACGTGAATAGTGTTTGTGGGTCCGGAGTT |
| 2 | AML1243KR8m2 | KS9 | GGATACCTTAACGCCGCCTATTGCTATGAGTAGTGTTTGTAGGTCTGGCATGCGAGT TGCACCCGTCTCGAAATC |
| 11 | AML1243KR8m2 s63 | KS9 | GGATACCTTAACGCGGCGTATTCCTATGAGTAGTGTTTGTAGGTCTGGCATGCGAGT TGCACC |
| 12 | AML1243KR8m2 s49 | KS9 | GGATACCTTAACGCCGCCTATTGGTATGAGTAGTGTTTGTAGGTCTGGC |

TABLE 2-continued

| SEQ ID NO | name | Modified base | Sequence |
|---|---|---|---|
| 13 | AML1243KR8m2 s49Fw_s20 | KS9 | TACCTTAACGCCGCCTATTGCTATGAGTAGTGTTTGTAGGTCTGGC |
| 14 | AML1243KR8m2 s49Fw_s15 | KS9 | TAACGCCGCCTATTGCTATGAGTAGTGTTTGTAGGTCTGGC |
| 3 | AML1243KR8m3 | KS9 | GGATACCTTAACGCCGCCTATTGCGAGGTGTGGCTAGTCGTTATAGGTCCACCGAGTTGCACCCGTCTCGAAATC |
| 15 | AML1243KR8m3 s63 | KS9 | GGATACCTTAACGCCGCGTATTGCGAGGTGTGGCTAGTCGTTATAGGTCCACCGAGTTGCACC |
| 16 | AML1243KR8m3 s63Fw_s20 | KS9 | TACCITAACGCCGCCTATTGCGAGGTGTGGCTAGTCGTTATAGGTCCACCGAGTTGCACC |
| 17 | AML1243KR8m3 s63Fw_s15 | KS9 | TAACGCCGCCTATTGCGAGGTGTGGCTAGTCGTTATAGGTCCACCGAGTTGCACC |

FIGS. 1A to 1F show predicted secondary structures of polynucleotides consisting of the following base sequences: SEQ ID NOs: 1 to 4 in FIG. 1A; SEQ ID NOs: 5 to 8 in FIG. 1B; SEQ ID NOs: 9 to 12 in FIG. 1C; SEQ ID NOs: 13 to 16 in FIG. 1D; SEQ ID NOs: 17 to 20 in FIG. 1E; and SEQ ID NOs: 21 and 22 in FIG. 1F. It is to be noted, however, that the present invention is not limited thereto.

In the binding nucleic acid molecule of the present invention, the polynucleotide encompasses, for example, at least one polynucleotide selected from the group consisting of the following polynucleotides (b) to (d).
(b) a polynucleotide that consists of a base sequence obtained by deletion, substitution, insertion, and/or addition of one or more bases in any of the base sequences of the polynucleotide (a) and binds to the α-amylase
(c) a polynucleotide that consists of a base sequence having at least 80% sequence identity to any of the base sequences of the polynucleotide (a) and binds to the α-amylase
(d) a polynucleotide that consists of a base sequence complementary to a polynucleotide hybridizing to any of the base sequences of the polynucleotide (a) under stringent conditions and binds to the α-amylase Regarding the polynucleotide (b), the term "one or more" is not limited as long as, for example, it is in the range where the polynucleotide (b) binds to α-amylase. The number of the "one or more" bases in any of the base sequences of the polynucleotide (a) is, for example, 1 to 10, 1 to 7, 1 to 5, 1 to 3, or 1 or 2. In the present invention, the numerical range regarding the number of bases, sequences, or the like discloses, for example, all the positive integers falling within that range. That is, for example, the description "one to five bases" discloses all of "one, two, three, four, and five bases" (the same applies hereinafter).

Regarding the polynucleotide (c), the "sequence identity" is not limited as long as, for example, it is in the range where the polynucleotide (c) binds to α-amylase. The sequence identity is, for example, at least 80%, at least 85%, at least 90%, at least 95%, at least 96%, at least 97%, at least 98%, or at least 99%. The sequence identity can be calculated with analysis software such as BLAST or FASTA using default parameters, for example (the same applies hereinafter).

Regarding the polynucleotide (d), the "polynucleotide hybridizing to" may be, for example, a polynucleotide that is perfectly or partially complementary to the polynucleotide (a) and binds to the α-amylase. The hybridization can be detected by various types of hybridization assay, for example. The hybridization assay is not particularly limited, and for example, a method described in "Molecular Cloning: A Laboratory Manual 2nd Ed." edited by Sambrook et al. (Cold Spring Harbor Laboratory Press [1989]) or the like can be employed.

Regarding the polynucleotide (d), the "stringent conditions" may be any of low stringency conditions, medium stringency conditions, and high stringency conditions, for example. The "low stringency conditions" are, for example, conditions where 5×SSC, 5×Denhardt's solution, 0.5% SDS, and 50% formamide are used at 32° C. The "medium stringency conditions" are, for example, conditions where 5×SSC, 5×Denhardt's solution, 0.5% SDS, and 50% formamide are used at 42° C. The "high stringency conditions" are, for example, conditions where 5×SSC, 5×Denhardt's solution, 0.5% SDS, and 50% formamide, are used at 50° C. Those skilled in the art can set the degree of stringency by, for example, setting the conditions such as the temperature, the salt concentration, the concentration and length of a probe, the ionic strength, the time, etc. as appropriate. As the "stringent conditions", it is also possible to employ conditions described in the above-described "Molecular Cloning: A Laboratory Manual 2nd Ed." edited by Sambrook et al. (Cold Spring Harbor Laboratory Press [1989]) or the like, for example.

The polynucleotides (a1) to (a3) are each a partial sequence of the polynucleotide (a). Thus, it can be said that they each define examples of the polynucleotide (b), (c), or (d), for example.

In the nucleic acid molecule of the present invention, the building blocks of the polynucleotide are, for example, nucleotide residues, examples of which include deoxyribonucleotide residues and ribonucleotide residues. The polynucleotide is, for example, a DNA consisting of deoxyribonucleotide residues or a DNA including a deoxyribonucleotide residue(s) and a ribonucleotide residue(s), and the polynucleotide may further include a non-nucleotide residue(s), as described below. The α-amylase-binding nucleic acid molecule of the present invention also may be referred to as "aptamer" hereinafter, for example.

The nucleic acid molecule according to the present invention may consist of any of the above-described polynucleotides, or may include any of the above-described polynucleotides, for example. In the latter case, the nucleic acid molecule of the present invention may include, for example, two or more polynucleotides selected from the above-described polynucleotides, as described below. The two or more polynucleotides may be the polynucleotides with the same sequence or different sequences. Also, in the latter case, the nucleic acid molecule of the present invention further may include a linker(s) and/or an additional sequence(s), for example. The linker is a sequence present between polynucleotides, for example. The additional sequence is a sequence added to an end, for example.

When the nucleic acid molecule according to the present invention includes, for example, a plurality of polynucleotides selected from the above-described polynucleotides, it is preferable that the plurality of polynucleotide sequences are linked to each other to form a single-stranded polynucleotide. The plurality of polynucleotide sequences may be linked to each other directly, or may be linked to each other indirectly with a linker, for example. It is preferable that the polynucleotide sequences are linked to each other directly or indirectly at their ends. When the nucleic acid molecule of the present invention includes the plurality of polynucleotide sequences, the number of the sequences is not particularly limited, and is, for example, 2 or more, 2 to 20, 2 to 10, or 2 or 3.

The length of the linker is not particularly limited, and is, for example, 1- to 200-mer, 1- to 20-mer, 3- to 12-mer, or 5- to 9-mer. The building blocks of the linker are, for example, nucleotide residues, examples of which include deoxyribonucleotide residues and ribonucleotide residues. The linker is not particularly limited, and examples thereof include polynucleotides such as a DNA consisting of deoxyribonucleotide residues and a DNA including a ribonucleotide residue(s). Specific examples of the linker include polydeoxythymine (poly[dT]), polydeoxyadenine (poly [dA]), and poly(dA-dT) having a repetitive sequence composed of A and T. Preferably, the linker is poly(dT) or poly(dA-dT).

In the nucleic acid molecule of the present invention, the polynucleotide is preferably a single-stranded polynucleotide. It is preferable that the single-stranded polynucleotide can form a stem structure and a loop structure by self-annealing, for example. It is preferable that the polynucleotide can form a stem-loop structure, an internal loop structure, and/or a bulge structure, for example.

The nucleic acid molecule of the present invention may be a double strand, for example. When the nucleic acid molecule is a double strand, for example, one of single-stranded polynucleotides includes the polynucleotide (a), a partial sequence thereof, or any of the polynucleotides (b) to (d), and the other single-stranded polynucleotide is not limited. The other single-stranded polynucleotide may be, for example, a polynucleotide including a base sequence complementary to any of the polynucleotides (a) to (d). When the nucleic acid molecule of the present invention is a double strand, it is preferable to dissociate the double strand to single-stranded polynucleotides by denaturation or the like before use, for example. Also, it is preferable that the dissociated single-stranded polynucleotide including any of the polynucleotides (a) to (d) is forming a stem structure and a loop structure as described above, for example.

In the present invention, the expression "can form a stem structure and a loop structure" encompasses that, for example, a stem structure and a loop structure are formed actually, and also, even if a stem structure and a loop structure are not formed, they can be formed depending on conditions. The expression "can form a stem structure and a loop structure (and grammatical variations thereof)" encompasses, for example, both the cases where the formation thereof has been confirmed through an experiment and where the formation thereof is predicted through simulation using a computer or the like.

The building blocks of the nucleic acid molecule of the present invention are, for example, nucleotide residues. Examples of the nucleotide residues include deoxyribonucleotide residues and ribonucleotide residues. The nucleic acid molecule of the present invention may be, for example, a DNA consisting of deoxyribonucleotide residues only or a DNA including one or more ribonucleotide residues. In the latter case, "one or more" is not particularly limited. For example, the number of the ribonucleotide residues in the polynucleotide is, for example, 1 to 91, 1 to 30, 1 to 15, 1 to 7, 1 to 3, or 1 or 2.

The polynucleotide may include, as a base in a nucleotide residue, a natural base or a modified base. The natural base (non-artificial base) is not particularly limited, and may be, for example, a purine base with a purine skeleton or a pyrimidine base with a pyrimidine skeleton. The purine base is not particularly limited, and examples thereof include adenine (a) and guanine (g). The pyrimidine base is not particularly limited, and examples thereof include cytosine (c), thymine (t), and uracil (u). Among them, cytosine (c) and thymine (t) are preferable.

When the polynucleotide includes the modified base(s), the site and the number of the modified bases are not particularly limited. In the polynucleotides shown in Tables 1A, 1B, and 2 above, it is preferable that, for example, the underlined thymines are modified bases, which specifically are modified thymines.

The modified base is a base modified with a modifying group, for example. The base to be modified with the modifying group (also referred to simply as the "base to be modified" hereinafter) is the natural base, for example. The modified base is not particularly limited, and may be, for example, a modified adenine, a modified guanine, a modified cytosine, a modified thymine, or a modified uracil, and is preferably a modified thymine.

In the modified base, the base to be modified may be modified with the modifying group either directly or indirectly, for example. In the latter case, the base to be modified may be modified with the modifying group via a linker, for example. The linker is not particularly limited.

In the base to be modified, a site to be modified with the modifying group is not particularly limited. When the base is a purine base, the modified site in the purine base may be, for example, the 7-position or the 8-position, preferably the 7-position of the purine skeleton. When the base is a pyrimidine base, the modified site in the pyrimidine base may be, for example, the 5-position or the 6-position, preferably the 5-position of the pyrimidine skeleton. Thymine has a methyl group bound to carbon at the 5-position. Thus, when the 5-position of the pyrimidine base is modified, for example, the modifying group may be bound to the carbon at the 5-position either directly or indirectly, or the modifying group may be bound to carbon in the methyl group bound to the carbon at the 5-position either directly or indirectly. When the pyrimidine skeleton has "=O" bound to carbon at the 4-position and a group that is not "—$CH_3$" or "—H" bound to carbon at the 5-position, the modified base can be referred to as a modified uracil or a modified thymine.

The modifying group is preferably an adenine residue or a substituted adenine residue, for example. That is, the modified base is preferably a base modified with the adenine residue or a base modified with the substituted adenine residue, for example. In the base to be modified, a site to be modified with the adenine residue or the substituted adenine residue is not particularly limited, and may be, for example, an amino group that binds to carbon at the 6-position of the adenine residue or the substituted adenine residue. The base to be modified with the adenine residue or the substituted adenine residue is not particularly limited, and is preferably a thymine, for example, and it is preferable that carbon in a methyl group bound to the carbon at the 5-position of the thymine is modified with the adenine residue or the substituted adenine residue.

When the modifying group is the adenine residue or the substituted adenine residue, it is preferable that, for example, the base to be modified is modified with the modifying group via the linker, as shown below.

[nucleotide residue]-[linker]-[adenine residue]

[nucleotide residue]-[linker]-[substituted adenine residue]

The linker is not particularly limited, and can be represented by, for example, each formula present between the nucleotide residue and the adenine residue/substituted adenine residue, as shown below. It is to be noted, however, that the linker is not limited thereto. In each formula, the numerical value "n" in $(CH_2)n$ is 1 to 10, 2 to 10, or 2, for example.

[nucleotide residue]=C—C(=O)—NH—$(CH_2)$n-[adenine residue]

[nucleotide residue]=C—C(=O)—NH—$(CH_2)$n-[substituted adenine residue]

[nucleotide residue]=C—C(=O)—NH—$CH_2$—$CH_2$-[adenine residue]

[nucleotide residue]=C—C(=O)—NH—$CH_2$—$CH_2$-[substituted adenine residue]

In each formula, one end of the linker [=C] forms a double bond with carbon of the base to be modified in the nucleotide residue, for example, and the other end of the linker [$CH_2$—] is bound to amine (—NH) in the adenine residue or the substituted adenine residue, for example.

The substituted adenine residue is, for example, a substituted adenine residue having a substituent. In the substituted adenine residue, the site substituted with the substituent is not particularly limited, and may be the 9-position or the 6-position of the adenine residue.

The substituent is not particularly limited, and may be, for example, an amidino aminoalkyl group, a trifluoromethyl group, a methylamino group, a dinitrophenyl group, or a lysyl group.

In the amidino aminoalkyl group, the alkyl group may be either linear or branched, for example. The number of carbon atoms in the alkyl group is not particularly limited, and is 1 to 12, 2 to 6, or 4, for example.

Specific examples of the amidino aminoalkyl group include a 4-amidino aminobutyl group and a 4-amidino aminoethyl group. Among them, the 4-amidino aminobutyl group is preferable.

Specific examples of a thymidine nucleotide residue modified with the adenine residue in the polynucleotide include a residue represented by the following formula (1) (also referred to as "KS9" hereinafter). Specific examples of a thymidine nucleotide residue modified with the substituted adenine residue in the polynucleotide include a residue represented by the following formula (2) (also referred to as "KK10" hereinafter). It is to be noted, however, that the present invention is not limited thereto.

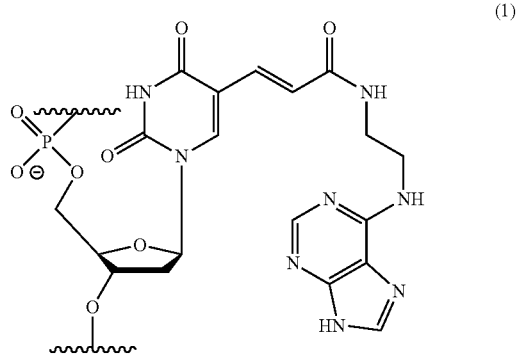

(1)

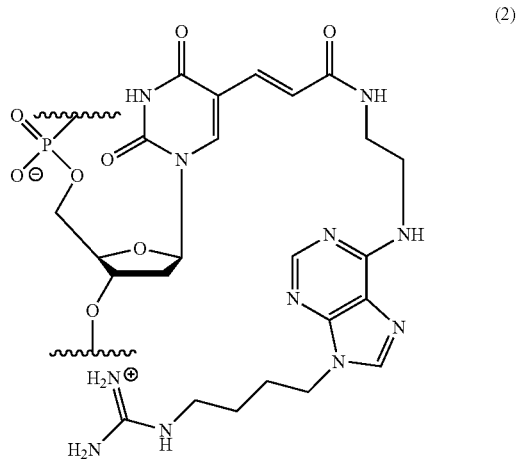

(2)

In the polynucleotides shown in Tables 1A, 1B, and 2 above, it is preferable that, for example, the underlined thymines are at least one of the nucleotide residues KS9 and KK10.

For example, when the nucleic acid molecule of the present invention includes the thymidine nucleotide residues, the polynucleotide can be synthesized using, as a monomer molecule, a nucleotide triphosphate represented by the following formula (3) (also referred to as "KS9 monomer" hereinafter) or a nucleotide triphosphate represented by the following formula (4) (also referred to as "KK10 monomer" hereinafter), for example. In the synthesis of the polynucleotide, for example, the monomer molecule binds to another nucleotide triphosphate via a phosphodiester bond.

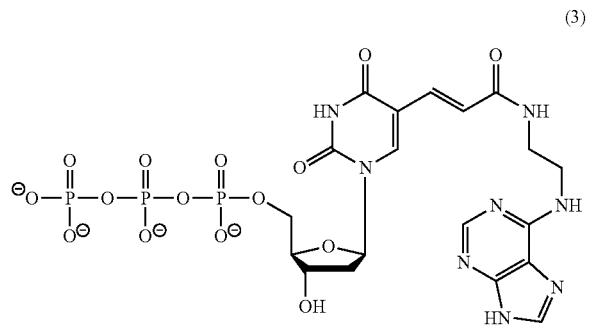

(3)

(4)

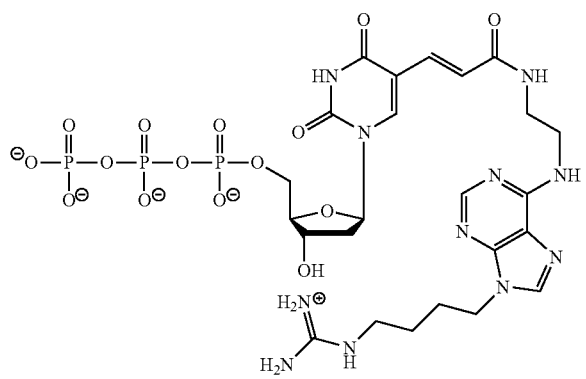

Other examples of the modifying group include methyl groups, fluoro groups, amino groups, thio groups, a benzylaminocarbonyl group, a tryptaminocarbonyl group, and an isobutylaminocarbonyl group.

Specific examples of the modified adenine include 7'-deazaadenine. Specific examples of the modified guanine include 7'-deazaguanine. Specific examples of the modified cytosine include 5'-methylcytosine (5-Me-dC). Specific examples of the modified thymine include 5'-benzylaminocarbonyl thymine, 5'-tryptaminocarbonyl thymine, and 5'-isobutylaminocarbonyl thymine. Specific examples of the modified uracil include 5'-benzylaminocarbonyl uracil (BndU), 5'-tryptaminocarbonyl uracil (TrpdU), and 5'-isobutylaminocarbonyl uracil. The modified uracils given above as examples also can be referred to as modified thymines.

The polynucleotide may include only one type or two or more types of the modified bases, for example.

The nucleic acid molecule of the present invention may include a modified nucleotide(s), for example. The modified nucleotide may be a nucleotide having the above-described modified base, a nucleotide having a modified sugar obtained through modification of a sugar residue, or a nucleotide having the modified base and the modified sugar.

The sugar residue is not particularly limited, and may be a deoxyribose residue or a ribose residue, for example. The modified site in the sugar residue is not particularly limited, and may be, for example, the 2'-position or the 4'-position of the sugar residue. Either one or both of the 2'-position and the 4'-position may be modified. Examples of a modifying group in the modified sugar include methyl groups, fluoro groups, amino groups, and thio groups.

When the base in the modified nucleotide residue is a pyrimidine base, it is preferable that the 2'-position and/or the 4'-position of the sugar residue is modified, for example. Specific examples of the modified nucleotide residue include modified nucleotide residues with the 2'-position of the deoxyribose residue or ribose residue being modified, such as a 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil nucleotide residue, 2'-aminated-cytosine nucleotide residue, 2'-thiated-uracil nucleotide residue, and 2'-thiated-cytosine nucleotide residue.

The number of the modified nucleotides is not particularly limited. For example, the number of the modified nucleotides in the polynucleotide is, for example, 1 to 100, 1 to 90, 1 to 80, or 1 to 70. Also, the number of the modified nucleotides in the full-length nucleic acid molecule including the polynucleotide is not particularly limited, and is, for example, 1 to 91, 1 to 78, or in the numerical ranges given above as examples of the number of the modified nucleotides in the polynucleotide.

The nucleic acid molecule of the present invention may include, for example, one or more artificial nucleic acid monomer residues. The term "one or more" is not particularly limited, and may be, for example, 1 to 100, 1 to 50, 1 to 30, or 1 to 10 in the polynucleotide, for example. Examples of the artificial nucleic acid monomer residue include peptide nucleic acids (PNAs), locked nucleic acids (LNAs), and 2'-0,4'-C-ethylenebridged nucleic acids (ENAs). The nucleic acid in the monomer residue is the same as described above, for example.

It is preferable that the nucleic acid molecule of the present invention is resistant to nuclease, for example. In order to allow the nucleic acid molecule of the present invention to have nuclease resistance, it is preferable that the nucleic acid molecule of the present invention includes the modified nucleotide residue(s) and/or the artificial nucleic acid monomer residue(s), for example. Also, in order to allow the nucleic acid molecule of the present invention to have nuclease resistance, the nucleic acid molecule of the present invention may have polyethylene glycol (PEG) of several tens of kDa, deoxythymidine, or the like bound to, e.g., the 5' end or the 3' end thereof.

The nucleic acid molecule of the present invention may further include an additional sequence, for example. Preferably, the additional sequence is bound to at least one of the 5' end and the 3' end, more preferably to the 3' end of the nucleic acid molecule, for example. The additional sequence is not particularly limited. The length of the additional sequence is not particularly limited, and is, for example, 1- to 200-mer, 1- to 50-mer, 1- to 25-mer, or 18- to 24-mer. The building blocks of the additional sequence are, for example, nucleotide residues, examples of which include deoxyribonucleotide residues and ribonucleotide residues. The additional sequence is not particularly limited, and examples thereof include polynucleotides such as a DNA consisting of deoxyribonucleotide residues and a DNA including a ribonucleotide residue(s). Specific examples of the additional sequence include poly(dT) and poly(dA).

The nucleic acid molecule of the present invention can be used in the state where it is immobilized on a carrier, for example. It is preferable to immobilize either the 5' end or the 3' end, more preferably the 3' end of the nucleic acid molecule of the present invention, for example. When the nucleic acid molecule of the present invention is immobilized, the nucleic acid molecule may be immobilized either directly or indirectly on the carrier, for example. In the latter case, it is preferable to immobilize the nucleic acid molecule via the additional sequence, for example.

The method for producing the nucleic acid molecule of the present invention is not particularly limited. For example, the nucleic acid molecule of the present invention can be synthesized by known methods such as: nucleic acid synthesis methods utilizing chemical synthesis; and genetic engineering procedures. The nucleic acid molecule of the present invention also can be obtained by a so-called SELEX method, for example. In this case, a target is preferably α-amylase.

The nucleic acid molecule of the present invention exhibits binding properties to the α-amylase, as described above. Thus, use of the nucleic acid molecule of the present invention is not particularly limited, as long as it is the use utilizing the binding properties of the nucleic acid molecule to the α-amylase. The nucleic acid molecule of the present invention can be used in various methods as an alternative to, e.g., an antibody against the α-amylase.

(2) α-Amylase Analysis Sensor

As described above, the analysis sensor of the present invention is an α-amylase analysis sensor characterized in that it includes the nucleic acid molecule of the present invention. It is only required that the analysis sensor of the present invention includes the nucleic acid molecule of the present invention, and other configurations are by no means limited. By using the analysis sensor of the present invention, the α-amylase can be detected by, for example, causing the nucleic acid molecule to bind to the α-amylase, as described above.

The analysis sensor of the present invention may be configured so that, for example, it further includes a carrier, and the nucleic acid molecule is disposed on the carrier. Preferably, the nucleic acid molecule is immobilized on the carrier. The type of the carrier and immobilization of the nucleic acid molecule are as described above, for example. The method for using the analysis sensor of the present invention is not particularly limited, and the above descriptions regarding the nucleic acid molecule of the present invention and the detection method of the present invention also apply to the analysis sensor of the present invention.

(3) Analysis Method

As described above, the analysis method of the present invention is a method including the step of: detecting α-amylase in a specimen by causing the specimen and a nucleic acid molecule to come into contact with each other, wherein the nucleic acid molecule is the α-amylase-binding nucleic acid molecule according to the present invention, and in the detection step, the nucleic acid molecule is caused to bind to the α-amylase in the specimen, and the α-amylase in the specimen is detected by detecting the binding. The analysis method of the present invention is characterized in that it uses the nucleic acid molecule of the present invention, and other steps, conditions, etc. are not particularly limited. In the analysis method of the present invention, the α-amylase analysis sensor of the present invention may be used as the nucleic acid molecule of the present invention.

The nucleic acid molecule of the present invention specifically binds to α-amylase. Thus, according to the present invention, it is possible to specifically detect α-amylase in a specimen by detecting the binding between the α-amylase and the nucleic acid molecule, for example. Specifically, since the present invention can analyze the presence or absence or the amount of α-amylase in a specimen, for example, it can be said that the present invention also can perform qualitative or quantitative analysis of the α-amylase.

In the present invention, the specimen is not particularly limited. Examples of the specimen include saliva, urine, plasma, and serum.

The specimen may be a liquid specimen or a solid specimen, for example. The specimen is preferably a liquid specimen from the viewpoint of ease of handling because the liquid specimen can be brought into contact with the nucleic acid molecule more easily, for example. In the case of the solid specimen, a liquid mixture, a liquid extract, a solution, or the like of the solid specimen prepared using a solvent may be used, for example. The solvent is not particularly limited, and may be water, physiological saline, or a buffer solution, for example.

The above-described detection step includes, for example: a contact step of causing the specimen and the nucleic acid molecule to come into contact with each other to cause the nucleic acid molecule to bind the α-amylase in the specimen; and a binding detection step of detecting the binding between the α-amylase and the nucleic acid molecule. The detection step may further include, for example, the step of analyzing the presence or absence or the amount of the α-amylase in the specimen on the basis of the result obtained in the binding detection step.

In the contact step, the method for causing the specimen and the nucleic acid molecule to come into contact with each other is not particularly limited. The contact between the specimen and the nucleic acid molecule is preferably achieved in a liquid, for example. The liquid is not particularly limited, and may be, for example, water, physiological saline, or a buffer solution.

In the contact step, the conditions under which the contact between the specimen and the nucleic acid molecule is caused are not particularly limited. The contact temperature is, for example, 4° C. to 37° C., or 18° C. to 25° C., and the contact time is, for example, 10 to 120 minutes or 30 to 60 minutes.

In the contact step, the nucleic acid molecule may be an immobilized nucleic acid molecule immobilized on a carrier or an unimmobilized nucleic acid molecule in a free state, for example. In the latter case, the nucleic acid molecule is brought into contact with the specimen in a container, for example. The nucleic acid molecule is preferably the immobilized nucleic acid molecule from the viewpoint of favorable handleability, for example. The carrier is not particularly limited, and may be, for example, a substrate, beads, or a container. The container may be a microplate or a tube, for example. The immobilization of the nucleic acid molecule is as described above, for example.

The binding detection step is the step of detecting the binding between the α-amylase in the specimen and the nucleic acid molecule, as described above. By detecting the presence or absence of the binding between the α-amylase and the nucleic acid molecule, it is possible to analyze the presence or absence of the α-amylase in the specimen (qualitative analysis), for example. Also, by detecting the degree of the binding (the amount of the binding) between the α-amylase and the nucleic acid molecule, it is possible to analyze the amount of the α-amylase in the specimen (quantitative analysis), for example.

In the case where the binding between the α-amylase and the nucleic acid molecule cannot be detected, it can be determined that no α-amylase is present in the specimen. In the case where the binding is detected, it can be determined that the α-amylase is present in the specimen.

The method for analyzing the binding between the α-amylase and the nucleic acid molecule is not particularly limited. A conventionally known method for detecting the binding between substances may be employed as the method, for example, and specific examples of the method include the above-described SPR. Detection of the binding may be detection of a complex of the α-amylase and the nucleic acid molecule, for example.

(4) Detection Kit

A detection kit according to the present invention is characterized in that it includes the α-amylase-binding nucleic acid molecule of the present invention. It is only required that the detection kit of the present invention includes the nucleic acid molecule of the present invention, and other configurations are by no means limited. By using the detection kit of the present invention, it is possible to perform the detection and the like of the α-amylase as described above, for example.

The detection kit of the present invention may include the sensor of the present invention as the nucleic acid molecule of the present invention, for example. The detection kit of the present invention further may include any component(s) in addition to the nucleic acid molecule of the present invention, for example. Examples of the component include the above-described carrier, a buffer solution, and instructions for use.

EXAMPLES

Next, examples of the present invention will be described. It is to be noted, however, that the present invention is by no means limited by the following examples. Commercially available reagents in the examples were used in accordance with their protocols, unless otherwise stated.

Example 1

The present example examined the binding ability and a kinetic parameter of each of aptamers represented by SEQ ID NOs: 1 to 22 to α-amylase by SPR.

(1) Aptamers

As aptamers of the present example, the following polynucleotides were synthesized. Aptamers of SEQ ID NOs: 1 to 17 and 22 are aptamers in which nucleotide residues including thymines underlined in Table 3A below are each a nucleotide residue represented by the above formula (1). Aptamers of SEQ ID NOs: 18 to 21 are aptamers in which nucleotide residues including thymines double-underlined in Table 3B below are each a nucleotide residue represented by the above formula (2).

TABLE 3A

| SEQ ID NO | name | Modified base | Sequence |
|---|---|---|---|
| 1 | AML1243KR8m1 | KS9 | GGATACCTTAACGCCGCCTATTGTGAACGACGTGAATAGTGTTTGTGGGTCCGGAGTTGCACCCGTCTCGAAATC |
| 2 | AML1243KR8m2 | KS9 | GGATACCTTAACGCCGCCTATTGCTATGAGTAGTGTTTGTAGGTCTGGCATGCGAGTTGCACCCGTCTCGAAATC |
| 3 | AML1243KR8m3 | KS9 | GGATACCTTAACGCCGCCTATTGCGAGGTGTGGCTAGTCGTTATAGGTCCACCGACTTGCACCCGTCTCGAAATC |
| 4 | AML1243KR8m4 | KS9 | GGATACCTTAACGCCGCCTATTGATTCTCTCTGACTAGTGTTTGTAGGTCGCAGAGTTGCACCCGTCTCGAAATC |
| 5 | AML1243KR8m5 | KS9 | GGATACCTTAACGCCGCCTATTGAGTTCAACAATGACTAGTGTTTGTCGGTCTGAGTTGCACCCGTCTCGAAATC |
| 6 | AML2243KR8m3 | KS9 | GGATACCTTAACGCCGCCTATTGGTGTCACTAGTGTTTGTCGGTGCCAGCAAGGAGTTGCACCCGTCTCGAAATC |
| 7 | AML1243KR8m1s65_FW_s20 | KS9 | TACCTTAACGCCGCCTATTGTGAACGACGTGAATAGTGTTTGTGGGTCCGGAGTTGCACCCG |
| 8 | AML1243KR8m1s65_FWs15 | KS9 | TAACGCCGCCTATTGTGAACGACGTGAATAGTGTTTGTGGGTCCGGAGTTGCACCCG |
| 9 | AML1243KR8m1s58_FW_s20 | KS9 | TACCTTAACGCCGCCTATTGTGAACGACGTGAATAGTGTTTGTGGGTCCGGAGTT |
| 10 | AML1243KR8m1s58_FW_s15 | KS9 | TAACGCCGCCTATTGTGAACGACGTGAATACTGTTTGTGGGTCCGGAGTT |
| 11 | AML1243KR8m2s63 | KS9 | GGATACCTTAACGCCGCCTATTGCTATGAGTAGTGTTTGTAGGTCTGGCATGCGAGTTGCACC |
| 12 | AML1243KR8m2s49 | KS9 | GGATACCTTAACGCCGCCTATTGCTATGAGTAGTGTTTGTAGGTCTCGC |
| 13 | AML1243KR8m2s49Fw_s20 | KS9 | TACCTTAACGCCGCCTATTGCTATGAGTAGTGTTTGTAGGTCTGGC |
| 14 | AML1243KR8q2549Fw_s15 | KS9 | TAACCCCGCCTATTCCTATGAGTAGTGTTTGTAGGTCTGGC |
| 15 | AML1243KR8m3s63 | KS9 | GGATACCTTAACGCCGCCTATTGCGAGGTGTGGCTAGTCGTTATAGGTCCACCGAGTTGCACC |
| 16 | AML1243KR8m3s63Fws20 | KS9 | TACCTTAACGCCGCCTATTGCGAGGTGTGGCTAGTCGTTATAGGTCCACCGAGTTGCACC |
| 17 | AML1243KR8m3s63Fw_s15 | KS9 | TAACGCCGCCTATTGCGAGGTGTGGCTAGTCGTTATAGGTCCACCGAGTTGCACC |
| 22 | AML1243KR8m1_KS9-3 mini | KS9 | GTGAACGACGTGAATAGTGTTTGTGGGTCCGGAGTT |

TABLE 3B

| SEQ ID NO | name | Modified base | Sequence |
|---|---|---|---|
| 18 | Amy_258KK10R8m1 | KK10 | GGTTACGCCCAGGACACATTTCAAAAGATGATGGCATACGTAAAGGGTCGAGGTAAG<br>CTCGGTCTCCTCGGATAATC |
| 19 | Amy_258KK10R8m2 | KK10 | GGTTACGCCCAGGACACATTTCATTGATGGCATACTAAGGGTCGAGGAATTCGTAAG<br>CTCGGTCTCCTCGGATAATC |
| 20 | Amy_258KK10R8m3 | KK10 | GGTTACGCCCAGGACACATTTCAGACCGTAAACAGTCCTGGTTGGCAAATGTGTAAG<br>CTCGGTCTCCTCGGATAATC |
| 21 | Amy_258KK10R8m4 | KK10 | GGTTACGCCCAGGACACATTTCTGTAGTGAAGTCCTGGTTGGCAAATTCATGGTAAG<br>CTCGGTCTCCTCGGATAATC |

To the 3' end of each of the aptamers, 20-mer polydeoxyadenine (poly[dA]) was added. Each of the thus-obtained poly(dA)-added aptamers was used in SPR to be described below.

(2) Specimen

Commercially available human α-amylase (Lee Biosolutions, hereinafter the same) was used as a specimen in a test to be described below.

(3) Analysis of Binding Ability by SPR

The analysis of the binding ability was carried out using a ProteON XPR36 (BioRad) in accordance with its instructions for use.

First, as a sensor chip designed specifically for the ProteON, a streptavidin-immobilized chip (trade name: ProteOn NLC Sensor Chip, BioRad) was set in the ProteON XPR36. Biotinylated poly(dT) at 5 μmol/L was injected to a flow cell of the sensor chip using ultrapure water (DDW), and the binding was allowed to proceed until the signal intensity (RU: Resonance Unit) reached about 900 RU. The biotinylated poly(dT) was prepared by biotinylating the 5' end of 20-mer deoxythymidine. Then, the poly(dA)-added aptamer at 200 nmol/L was injected to the flow cell of the chip using an SPR buffer at a flow rate of 25 μL/min for 80 seconds, and the binding was allowed to proceed until the signal intensity reached about 800 RU. This result, which corresponds to the signal indicating the amount of the aptamer immobilized on the sensor chip, is referred to as an "aptamer immobilization measured value (A)". Subsequently, the specimen was injected using the SPR buffer at a flow rate of 50 μL/min for 120 seconds, followed by washing performed by flowing the SPR buffer under the same conditions for 300 seconds. The concentration of the human α-amylase in the specimen was set to 400 nmol/L. Signal intensity measurement was performed concurrently with the injection of the specimen and the washing with the SPR buffer. With 0 seconds being the start of the injection, the mean value of signal intensities from 115 seconds to 125 seconds was determined. This result, which corresponds to the signal indicating the amount of the binding between the aptamer and the protein, is referred to as a "protein binding measured value (B)". Then, the value (B/A) obtained by dividing the protein binding measured value (B) by the aptamer immobilization measured value (A) was determined as a relative value (Relative Unit). As Comparative Examples 1-1 and 1-2, the signal intensity measurement was performed in the same manner using, instead of the poly(dA)-added aptamer, a negative control 1 (SEQ ID NO: 23) and a negative control 2 (SEQ ID NO: 24) exhibiting no binding properties to α-amylase, respectively.

Negative control 1 (KS9 random pool)
GGATACCTTAACGCCGCCTATTGNNNNNNNNNNNNNNNNNNNNNNNNNNNNNNNGAGTTGCACCCGTCTCGAAATC Negative control 2 (KK10 random pool)
GGTTACGCCCAGGACACATTTCNNNNNNNNNNNNNNNNNNNNNNNNNNNNNNNGTAAGCTCGGTCTCCTCGGATAATC The composition of the SPR buffer was as follows: 40 mmol/L HEPES, 125 mmol/L NaCl, 5 mmol/L KCl, 1 mmol/L MgCl$_2$, and 0.01% Tween® 20. The pH of the SPR buffer was set to 7.4.

Figure 2A:
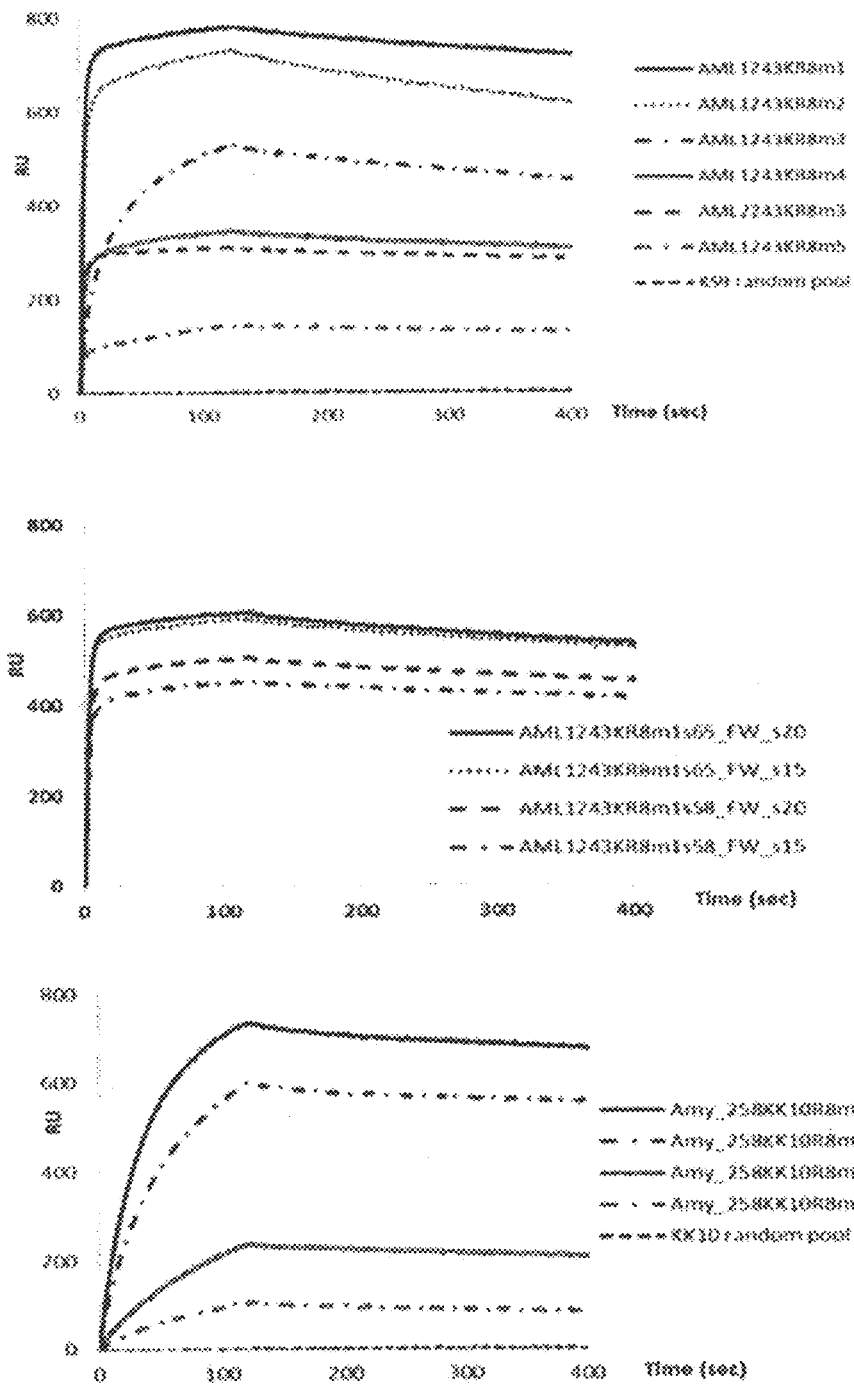
FIG. 2A shows graphs showing the binding ability of aptamers to α-amylase in Example 1 of the present invention.
Figure 2B:
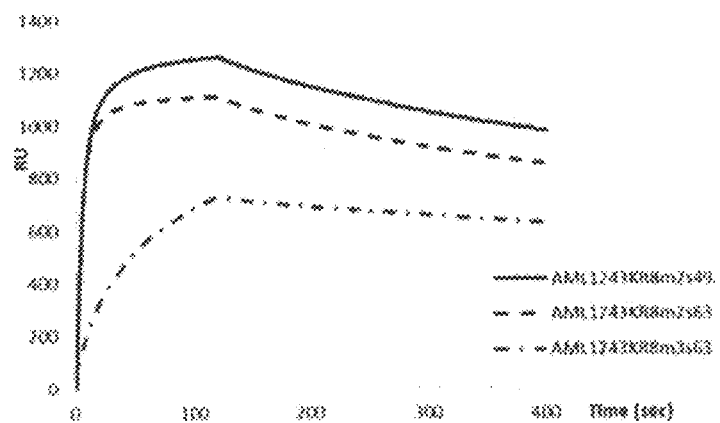
FIG. 2B shows graphs showing the binding ability of other aptamers to the α-amylase in Example 1 of the present invention.
Figure 2B:
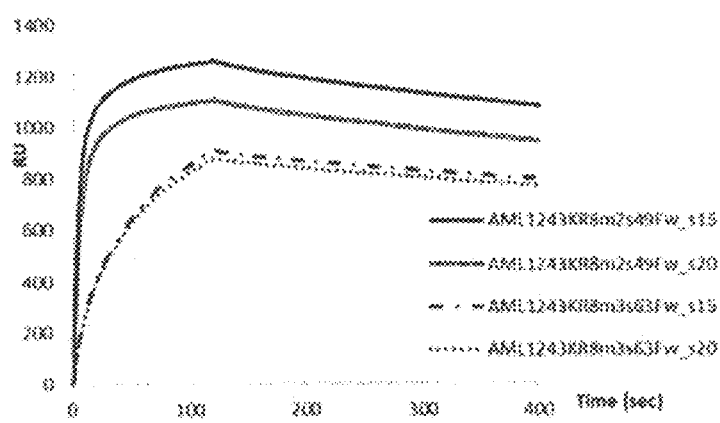
Figure 2B:
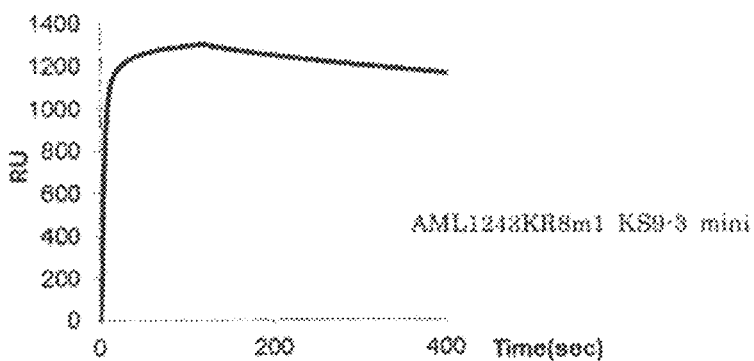
Figure 3:
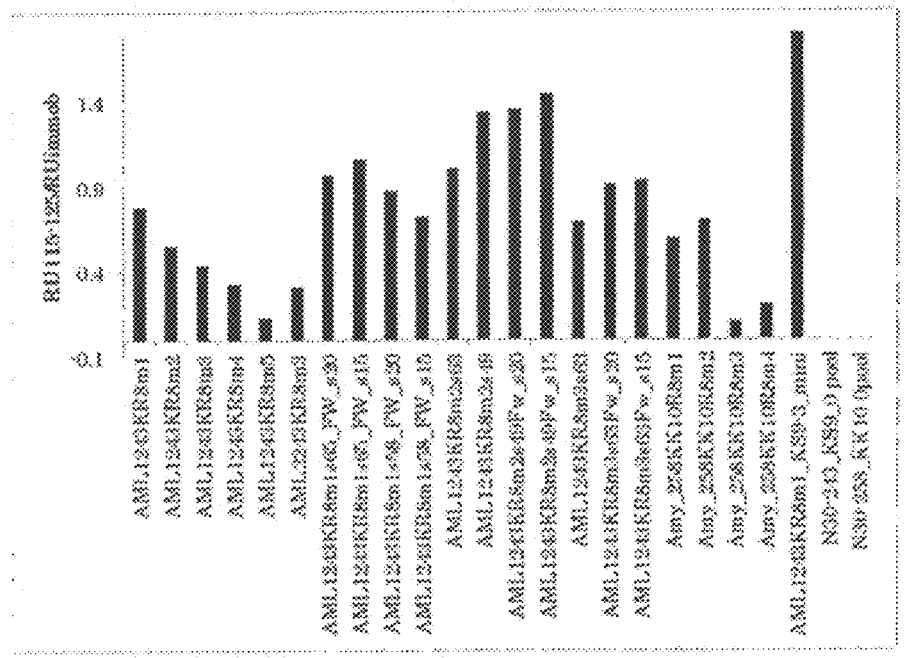
FIG. 3 is a graph showing relative values of the binding ability of the aptamers to the α-amylase in Example 1 of the present invention.

The results obtained are shown in FIGS. 2A, 2B, and 3. FIGS. 2A and 2B show graphs showing the binding ability of the aptamers to the α-amylase. The horizontal axis indicates the measurement time (second), and the vertical axis indicates the signal intensity (RU). In the horizontal axis, the time from 0 to 120 seconds corresponds to the specimen injection time, and the time after 120 seconds corresponds to the time for washing with the SPR buffer (the same applies hereinafter). FIG. 3 is a graph showing the relative value (B/A) of the binding ability. In FIG. 3, the horizontal axis indicates the type of the aptamer, and the vertical axis indicates the relative value.

As can be seen from FIGS. 2A, 2B, and 3, the aptamers according to the present example all exhibited binding properties to the human α-amylase. In particular, as can be seen from FIG. 3, the aptamer of SEQ ID NO: 22 (AML1243KR8m1_KS9-3_mini) exhibited excellent binding properties. In contrast, the negative controls 1 and 2 did not exhibit binding properties to the human α-amylase.

Example 2

The present example examined the binding ability (dissociation constant) of the aptamers of SEQ ID NOs: 1 to 3, 7 to 19, 21, and 22 to α-amylase by SPR.

The binding ability of the aptamers was analyzed by SPR in the same manner as in Example 1, except that the concentration of the α-amylase in the specimen was set to a plurality of values. The concentration was set to 20 nmol/L, 10 nmol/L, 5 nmol/L, 2.5 nmol/L, and 1.25 nmol/L. Then, from the results obtained by the SPR analysis, the kinetic parameter and the chi-squared value were calculated. The results obtained are shown in Table 4 below. As can be seen from Table 4 below, the dissociation constants (KD) of all these aptamers were 17 nM or less, from which it was found that these aptamers all exhibit excellent binding properties to human α-amylase.

TABLE 4

| SEQ ID NO | name | Kd (M) | Chi2 |
|---|---|---|---|
| 1 | AML1243KR8m1 | 8.05E−10 | 4.3 |
| 2 | AML1243KR8m2 | 2.60E−09 | 23.87 |
| 3 | AML1243KR8m3 | 1.99E−08 | 31.8 |
| 7 | AML1243KR8m1s65_FW_s20 | 6.8E−10 | 4.17 |
| 8 | AML1243KR8m1s65_FW_s15 | 4.47E−10 | 5.18 |
| 9 | AML1243KR8m1s58_FW_s20 | 7.07E−10 | 3.26 |
| 10 | AML1243KR8m1s58_FW_s15 | 3.58E−10 | 2.68 |
| 11 | AML1243KR8m2s63 | 3.93E−09 | 17.73 |
| 12 | AML1243KR8m2s49 | 3.19E−09 | 18.8 |
| 13 | AML1243KR8m2s49Fw_s20 | 4.23E−09 | 24.85 |
| 14 | AML1243KR8m2s49Fw_s15 | 2.66E−09 | 24.55 |
| 15 | AML1243KR8m3s63 | 1.64E−08 | 23.63 |
| 16 | AML1243KR8m3s63Fw_s20 | 1.66E−08 | 29.33 |
| 17 | AML1243KR8m3s63Fw_s15 | 1.87E−08 | 30.79 |
| 18 | Amy_258KK10R8m1 | 2.72E−09 | 3.85 |
| 19 | Amy_258KK10R8m2 | 2.30E−09 | 5.05 |
| 21 | Amy_258KK10R8m4 | 7.34E−09 | 5.69 |
| 22 | AML1243KR8m1_KS9-3_mini | 6.07E−10 | 10.58 |

Example 3

The present example examined the binding ability of aptamers of the present invention to α-amylase by capillary electrophoresis (referred to as "CAE" hereinafter).

(1) Aptamers

The 5' end of each of the aptamers of SEQ ID NOs: 1, 2, 3, and 19 was labeled with a fluorescent substance (TYE665, manufactured by IDT). The thus-obtained labeled aptamers were used in the present example. Also, as a negative control (NC), a labeled aptamer obtained by labeling the 5' end of the negative control 1 (SEQ ID NO: 23) used in Example 1 in the same manner was used.

(2) Specimen

The commercially available human α-amylase or human saliva was used as a specimen in an experiment to be described below.

(3) Binding Ability Analysis 1 by CAE

Reaction solutions containing the labeled aptamer (SEQ ID NO: 1) were prepared. Each of the reaction solutions was subjected to CAE under the following conditions. The reaction solution was caused to migrate while separating the components therefrom, and the fluorescence at a maximum absorption wavelength (665 nm) of the fluorescent substance was measured. As the reaction solutions, the following four types of reaction solutions were used: a reaction solution 1 containing the labeled aptamer only; a reaction solution 2 containing the labeled aptamer and the α-amylase; a reaction solution 3 containing the labeled aptamer and the saliva; and a reaction solution 4 containing the labeled aptamer as the negative control and the saliva. In each of the reaction solutions, the concentration of the labeled aptamer was 200 nmol/L. In the reaction solution 2, the concentration of the α-amylase was 2 μmol/L. In the reaction solutions 3 and 4, the concentration of the saliva was 10%. The reminder of each of the reaction solutions was a buffer solution. The composition of the buffer solution was as follows: 40 mmol/L HEPES (pH 7.5), 125 mmol/L NaCl, 5 mmol/L KCl, and 1 mmol/L $MgCl_2$.

Figure 4:
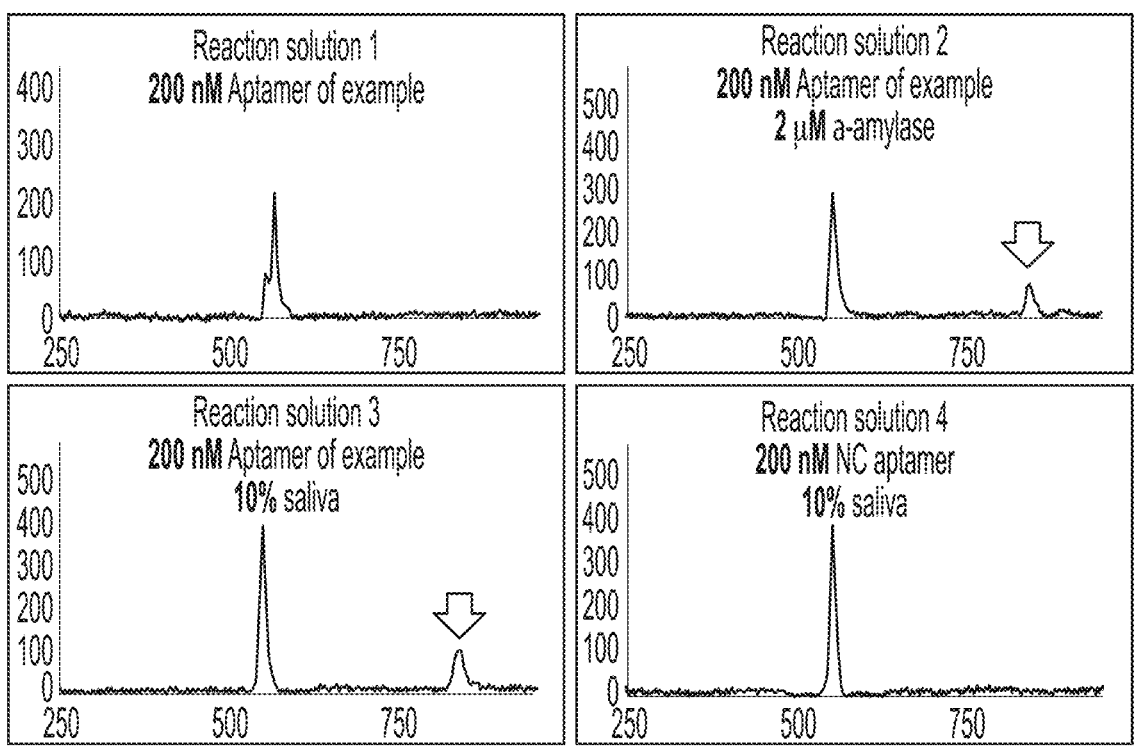
FIG. 4 shows chromatograms showing the binding ability of an aptamer to α-amylase in respective reaction solutions in Example 3 of the present invention.

(Conditions of CAE)
Measurement Device: Cosmo-i SV1210 (Hitachi High-Technologies Corporation)
Measurement chip: i-chip 12 (Hitachi Chemical Company, Ltd.)
Electrophoresis gel: 0.6% hydroxypropyl methylcellulose (viscosity: 2.600-5.600, Sigma Chemical Co., # H7509)
Gel dissolving buffer: 40 mmol/L HEPES (pH 7.5), 5 mmol/L KCl, 1 mmol/L $MgCl_2$
Injection voltage: 600 V
Injection time: 120 seconds
Separation voltage: 350 V
Separation time: 240 seconds The results obtained are shown in FIG. 4. FIG. 4 shows chromatograms showing the binding ability of the aptamer to the α-amylase in the respective reaction solutions. The horizontal axis indicates the electrophoresis time (second), and the vertical axis indicates the signal intensity.

As can be seen from FIG. 4, when the reaction solution 1 containing only the labeled aptamer of the example was used, one peak was observed. This peak is a peak derived from the labeled aptamer unbound to the target. In contrast, when the reaction solution 2 containing the α-amylase and the reaction solution 3 containing the saliva were used, the chromatograms each showed a peak at the same electrophoresis time (A1) as in the case where the reaction solution 1 was used and also showed another peak (indicated with the arrow in each chromatogram) at an electrophoresis time (A2) later than the electrophoresis time (A1). The aptamer carrying the target bound thereto has a larger molecular weight than the aptamer unbound to the target. Accordingly, it can be said that the peaks at the electrophoresis time (A2) observed when the reaction solutions 2 and 3 were used were each derived from the complex of the labeled aptamer and the α-amylase. When the reaction solution 4 containing the negative control (NC) was used, a peak was observed only at the same electrophoresis time (A1) as in the case where the reaction solution 1 was used. This indicates that the aptamer did not bind to the α-amylase.

(4) Binding Ability Analysis 2 by CAE

Preparation of the reaction solution 2 and the binding ability analysis by CAE were carried out in the same manner as in the above item (3), except that the labeled aptamers (SEQ ID NOs: 1, 2, 3, and 19) were used. Further, in order to examine the specificity of the labeled aptamers to the α-amylase, the binding ability analysis by CAE was performed in the same manner as in the case where the above-described reaction solution 2 was used, except that, instead of the α-amylase, human chromogranin A (CgA, recombinant full length protein, Creative BioMart, # CHGA-26904TH) or human IgA (secretory, Biomedicals, LLC-Cappel Products, #55905), each having a His-tag fused at the N terminus were used.

Figure 5:
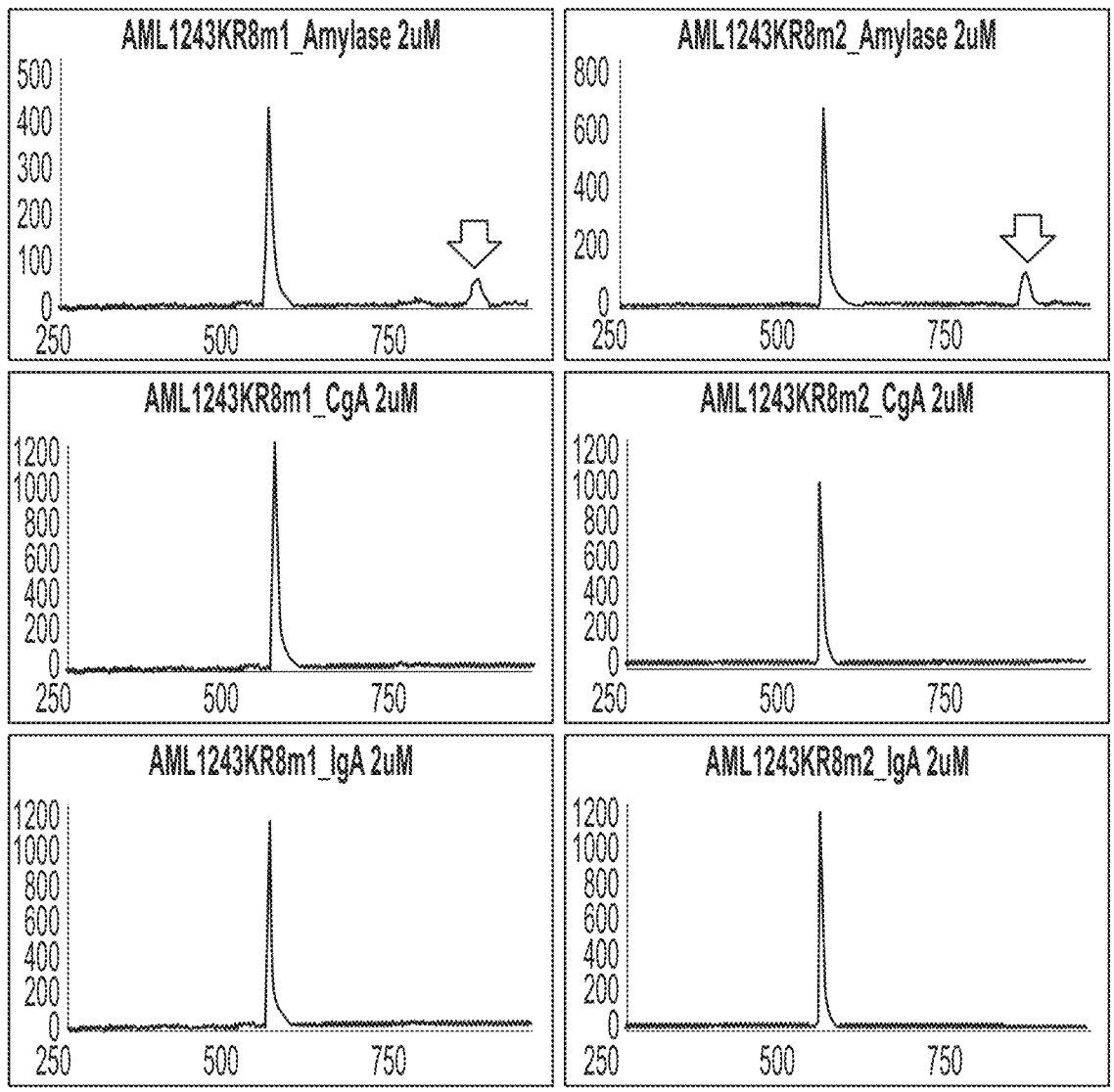
FIG. 5 shows chromatograms showing the binding ability of aptamers to targets in respective reaction solutions in Example 3 of the present invention.
Figure 6:
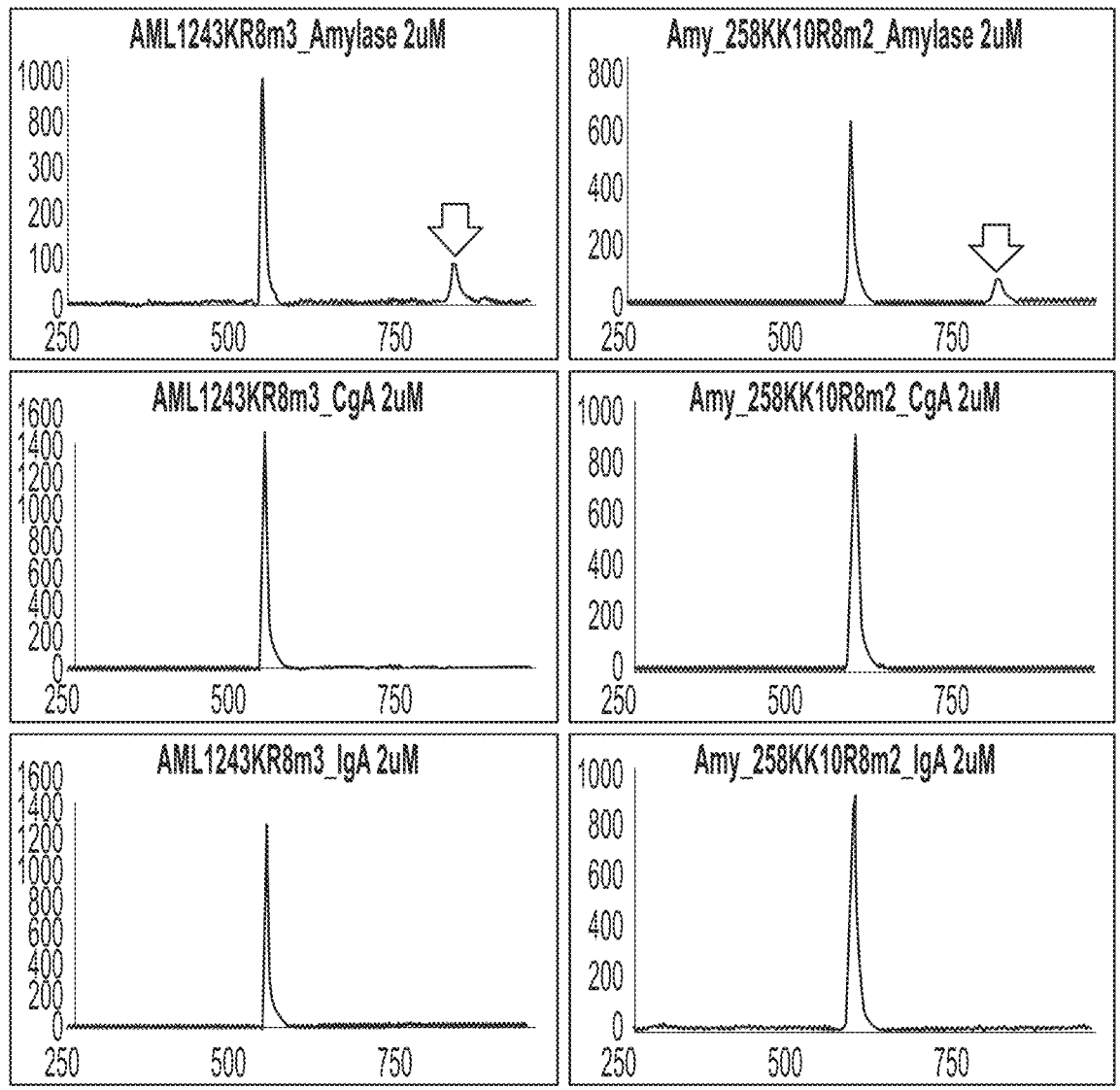
FIG. 6 shows chromatograms showing the binding ability of other aptamers to the targets in the respective reaction solutions in Example 3 of the present invention.

The results obtained are shown in FIGS. 5 and 6. FIGS. 5 and 6 show chromatograms showing the binding ability of the aptamers to the targets (α-amylase, chromogranin, and IgA) in the respective reaction solutions. The horizontal axis indicates the data point (corresponding to the electrophoresis time), and the vertical axis indicates the signal intensity.

As can be seen in FIGS. 5 and 6, regarding all the labeled aptamers of the present example, when the reaction solution containing the α-amylase was used, a peak was observed at an electrophoresis time different from that at which the peak derived from the aptamer unbound to the target was observed. In contrast, when the reaction solution containing the chromogranin or the IgA was used, a peak was observed only at the electrophoresis time indicating the peak of the aptamer that unbound to the target. These results demonstrate that the aptamers of the present example exhibit binding properties specifically to the human α-amylase.

Example 4

The present example examined the binding ability of the aptamer of SEQ ID NO: 1 to α-amylase by a pull-down assay using magnetic beads.

(1) Aptamer-Bound Beads

SA beads (Invitrogen Corporation, trade name: MyOne-SA C1), which are magnetic beads having streptavidin (SA) bound to their surfaces, were provided, and the aptamer was caused to bind to the SA beads to prepare aptamer-bound beads. More specifically, the aptamer-bound beads were prepared in the following manner. First, a complementary strand 100% complementary to the aptamer was prepared. On the other hand, a 5' region sequence (SEQ ID NO: 25, GGATACCTTAACGCCGCCTATTG) of the aptamer was provided, and the 5' end thereof was biotinylated to prepare a biotinylated primer. Then, amplification by PCR was performed using the biotinylated primer with the complementary strand as a template, whereby the aptamer with the 5' end thereof being biotinylated was synthesized. A double strand composed of the synthesized aptamer and the complementary strand was reacted with the SA beads, thereby causing biotin in the double strand to bind to avidin in the SA beads. Subsequently, by an alkali treatment of the complexes of the double strands and the SA beads with NaOH, each double strand was dissociated to remove the complementary strand. Through the above-described process, the aptamer-bound beads, which are the SA beads having the biotinylated aptamers bound thereto via biotin-avidin binding, were prepared.

(2) Specimen

Human saliva was used as a specimen in an experiment to be described below.

(3) Pull-Down Assay The aptamer-bound beads (final concentration: 10 mg/mL) and the specimen (final concentration: 90%) were mixed together in an SB1T buffer solution (40 mmol/L HEPES, 125 mmol/L NaCl, 5 mmol/L KCl, 1 mmol/L $MgCl_2$, and 0.01% Tween® 20, pH 7.4). This reaction solution was allowed to react at room temperature for 30 minutes. The reaction solution was centrifuged to collect the beads, and the beads were subjected to centrifugal washing with the SB1T buffer solution three times. In the case where the aptamer has bound to α-amylase, the beads carry the α-amylase bound thereto via the aptamer. Thus, the α-amylase was released from the beads by mixing the beads in an SDS buffer solution and heat-treating the SDS buffer solution at 95° C. for 10 minutes. Then, the beads were removed from the SDS buffer solution after the heat treatment, and the SDS buffer solution was subjected to SDS-PAGE using a PAGEL (C520L, ATTO Corporation). As a buffer for electrophoresis, the SDS buffer was used. The composition of the SDS buffer was as follows: 25 mmol/L Tris, 192 mmol/L glycine, and 0.1% SDS.

Next, the gel after being subjected to the SDS-PAGE was stained using a GelCode Blue Stain Reagent (Thermo SCIENTIFIC). As a molecular-weight marker, a Bench Mark Protein Ladder (Invitrogen Corporation) was used. Further, as a control 1, SDS-PAGE and detection were carried out in the same manner, except that, instead of the aptamer-bound beads, the SA beads having the biotinylated primer bound thereto were used. Further, as a control 2, SDS-PAGE and detection were carried out with respect to the human α-amylase.

Figure 7:
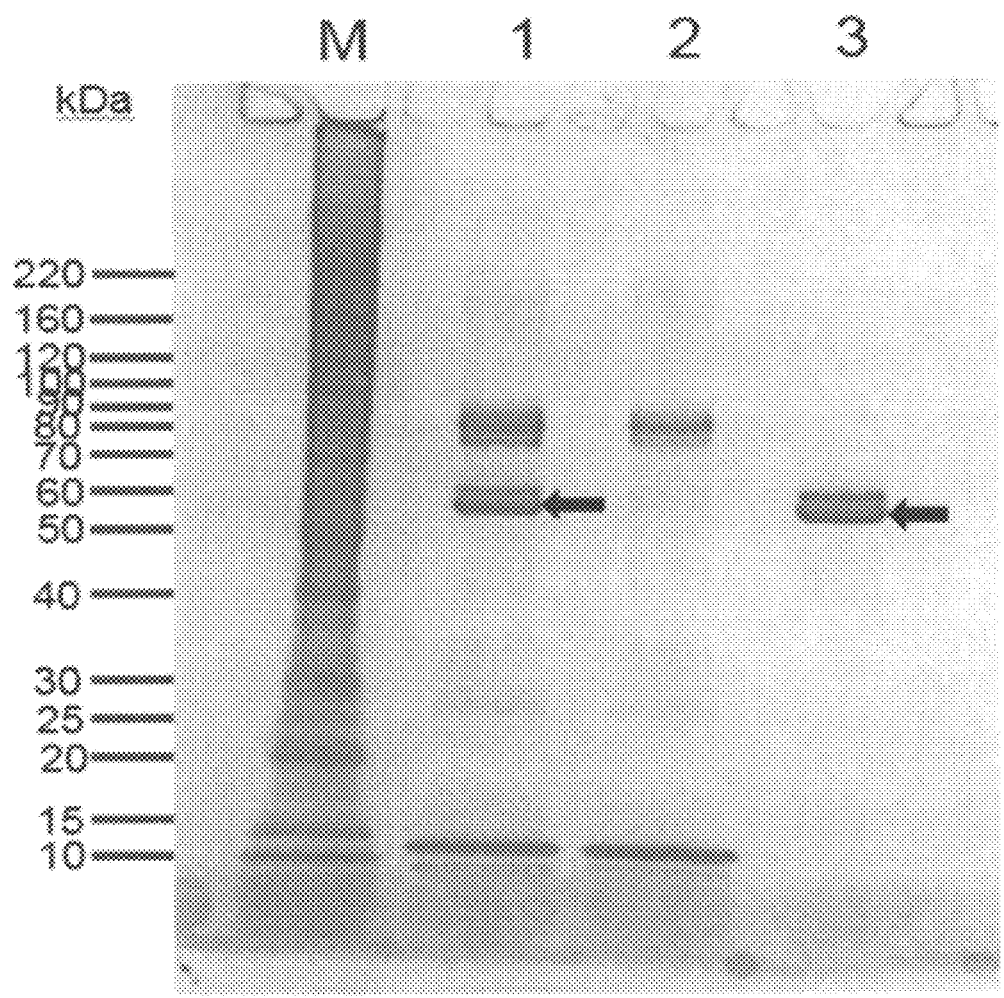
FIG. 7 is a photograph showing the results of SDS-PAGE in Example 4 of the present invention.

The results obtained are shown in FIG. 7. FIG. 7 is a photograph showing the results of the SDS-PAGE with respect to the proteins released from the aptamer-bound beads. In FIG. 7, the molecular weight is shown on the left side of the photograph, Lane M shows the molecular-weight marker (M), Lane 1 shows the result obtained when the aptamer-bound beads having the aptamer of the example bound thereto, Lane 2 shows the result obtained when the SA beads having the primer bound thereto were used, and Lane 3 shows the result obtained when the human α-amylase was used.

As can be seen from FIG. 7, in Lane 1 showing the result obtained when the aptamer-bound beads were used, the band was observed at the same site as in Lane 3 showing the result obtained when the α-amylase was used (see the bands indicated with the arrows in FIG. 7). On the other hand, when the primer-bound beads were used, the band was not observed at the same site as when the α-amylase was used.

Thus, whether the band in Lane 1 was derived from the α-amylase was examined in the following manner using a liquid chromatograph mass spectrometer LCMS-IT-TOF (Shimadzu Corporation). First, in the gel shown in FIG. 7, the band indicated with an arrow in Lane 1 was excised, and cut into square pieces of 1 mm×1 mm. The gel pieces were digested with trypsin, and then dissolved in 10 μL of a mobile phase A solution to obtain a dissolved sample. The dissolved sample was subjected to liquid chromatography (LC) under the following conditions. Then, components of the sample separated by LC were analyzed through search in MS/MS Ions Search under the following conditions. For the search, Mascot (Matrix Science) was used as a database search engine, and NCBI database was used. During the search, Homo sapience (human) was designated as a biological species. In this search, the Mascot score indicates the probability of a candidate protein, and the candidate protein exhibiting the highest Mascot score can be identified as the protein being analyzed.

(Experimental Conditions of LC)
Column: PicoFrit column BetaBasic C18 (manufactured by New Objective)
Mobile phase A solution: 0.1% formic acid/2% acetonitrile
Mobile phase B solution: 0.1% formic acid/80% acetonitrile
Gradient:
  0-30 minutes: 5%-40% B solution
  30-40 minutes: 40%-100% B solution
  40-60 minutes: 100% B solution
Flow rate: 300 nL/min
(Experimental conditions of MS)
Ionization mode nanoESI+
MS measurement range: MS1 m/z 400-1500, MS2 m/z 50-1500×3
Data-Dependent-Scan Mode As a result, it was found that the protein of the band in Lane 1 had a theoretical mass of 58398 and exhibited a high Mascot score of 1638 for human α-amylase. From this result, it was confirmed that the protein of the band in Lane 1 was human α-amylase.

From these results, it was found that the aptamer of the present example exhibits binding properties to the human α-amylase.

This application claims priority from Japanese Patent Application No. 2015-222952 filed on Nov. 13, 2015. The entire disclosure of this Japanese patent application is incorporated herein by reference.

INDUSTRIAL APPLICABILITY

The α-amylase-binding nucleic acid molecule of the present invention can bind to α-amylase with the above-described dissociation constant. Thus, the α-amylase-binding nucleic acid molecule of the present invention can detect α-amylase in a specimen with high accuracy on the basis of the presence or absence of the binding with the α-amylase, for example. Therefore, it can be said that the α-amylase-binding nucleic acid molecule of the present invention is a very useful tool for the detection of α-amylase in the fields of preventive medicine, health care, pathological diagnosis of diseases such as pancreas cancer and diabetes, diagnosis of stress, and the like, for example.

SEQUENCE LISTING

TF15019WO_ST25.txt

The invention claimed is:

1. An α-amylase-binding nucleic acid molecule comprising the following polynucleotide (a) or (c):
   (a) a polynucleotide consisting of any of base sequences of SEQ ID NOs: 1 to 22; and
   (c) a polynucleotide that consists of a base sequence having at least 80% sequence identity to any of the base sequences of the polynucleotide (a) and binds to the α-amylase.

2. The α-amylase-binding nucleic acid molecule according to claim 1, wherein
   the α-amylase-binding nucleic acid molecule comprises a modified base, which is a base modified with a modifying group.

3. The α-amylase-binding nucleic acid molecule according to claim 2, wherein
   the modified base is a modified thymine.

4. The α-amylase-binding nucleic acid molecule according to claim 2, wherein
   the modifying group is an adenine residue or a substituted adenine residue.

5. The α-amylase-binding nucleic acid molecule according to claim 4, wherein
   the substituted adenine residue has a substituent bound to N at a 9-position.

6. The α-amylase-binding nucleic acid molecule according to claim 5, wherein
   the substituent is an amidino aminoalkyl group.

7. The α-amylase-binding nucleic acid molecule according to claim 6, wherein the amidino aminoalkyl group is a 4-amidino aminobutyl group.

8. The α-amylase-binding nucleic acid molecule according to claim 2, wherein
   the modified base is a modified purine base with a 7-position of a purine base being modified with the modifying group or a modified pyrimidine base with a 5-position of a pyrimidine base being modified with the modifying group.

9. The α-amylase-binding nucleic acid molecule according to claim 2, wherein
   the polynucleotide is a DNA.

10. An α-amylase analysis sensor comprising:
    the α-amylase-binding nucleic acid molecule according to claim 1.

11. An α-amylase analysis method comprising the step of:
    detecting α-amylase in a specimen by causing the specimen and a nucleic acid molecule to come into contact with each other,
    wherein the nucleic acid molecule is the α-amylase-binding nucleic acid molecule according to claim 1, and
    in the detection step, the nucleic acid molecule is caused to bind to the α-amylase in the specimen, and the α-amylase in the specimen is detected by detecting the binding.

12. The α-amylase analysis method according to claim 11, wherein
    the specimen is at least one selected from the group consisting of saliva, urine, plasma, and serum.

* * * * *

```
                        SEQUENCE LISTING

<160> NUMBER OF SEQ ID NOS: 25

<210> SEQ ID NO 1
<211> LENGTH: 75
<212> TYPE: DNA
<213> ORGANISM: Artificial Sequence
<220> FEATURE:
<223> OTHER INFORMATION: aptamer

<400> SEQUENCE: 1
ggatacctta acgccgccta ttgtgaacga cgtgaatagt gtttgtgggt ccggagttgc    60
acccgtctcg aaatc                                                    75

<210> SEQ ID NO 2
<211> LENGTH: 75
<212> TYPE: DNA
<213> ORGANISM: Artificial Sequence
<220> FEATURE:
<223> OTHER INFORMATION: aptamer

<400> SEQUENCE: 2
ggatacctta acgccgccta ttgctatgag tagtgtttgt aggtctggca tgcgagttgc    60
acccgtctcg aaatc                                                    75

<210> SEQ ID NO 3
<211> LENGTH: 75
<212> TYPE: DNA
<213> ORGANISM: Artificial Sequence
<220> FEATURE:
<223> OTHER INFORMATION: aptamer

<400> SEQUENCE: 3
ggatacctta acgccgccta ttgcgaggtg tggctagtcg ttataggtcc accgagttgc    60
acccgtctcg aaatc                                                    75

<210> SEQ ID NO 4
<211> LENGTH: 75
<212> TYPE: DNA
<213> ORGANISM: Artificial Sequence
<220> FEATURE:
<223> OTHER INFORMATION: aptamer

<400> SEQUENCE: 4
ggatacctta acgccgccta ttgattctct gtgactagtg tttgtaggtc gcagagttgc    60
acccgtctcg aaatc                                                    75

<210> SEQ ID NO 5
<211> LENGTH: 75
<212> TYPE: DNA
<213> ORGANISM: Artificial Sequence
<220> FEATURE:
<223> OTHER INFORMATION: aptamer

<400> SEQUENCE: 5
ggatacctta acgccgccta ttgagttcaa caatgactag tgtttgtcgg tctgagttgc    60
acccgtctcg aaatc                                                    75
```

```
<210> SEQ ID NO 6
<211> LENGTH: 75
<212> TYPE: DNA
<213> ORGANISM: Artificial Sequence
<220> FEATURE:
<223> OTHER INFORMATION: aptamer

<400> SEQUENCE: 6 ggataccttta acgccgccta ttggtgtcac tagtgtttgt cggtgccagc aaggagttgc    60
acccgtctcg aaatc                                                      75

<210> SEQ ID NO 7
<211> LENGTH: 62
<212> TYPE: DNA
<213> ORGANISM: Artificial Sequence
<220> FEATURE:
<223> OTHER INFORMATION: aptamer

<400> SEQUENCE: 7
taccttaacg ccgcctattg tgaacgacgt gaatagtgtt tgtgggtccg gagttgcacc    60
cg                                                                    62

<210> SEQ ID NO 8
<211> LENGTH: 57
<212> TYPE: DNA
<213> ORGANISM: Artificial Sequence
<220> FEATURE:
<223> OTHER INFORMATION: aptamer

<400> SEQUENCE: 8
taacgccgcc tattgtgaac gacgtgaata gtgtttgtgg gtccggagtt gcacccg       57

<210> SEQ ID NO 9
<211> LENGTH: 55
<212> TYPE: DNA
<213> ORGANISM: Artificial Sequence
<220> FEATURE:
<223> OTHER INFORMATION: aptamer

<400> SEQUENCE: 9
taccttaacg ccgcctattg tgaacgacgt gaatagtgtt tgtgggtccg gagtt         55

<210> SEQ ID NO 10
<211> LENGTH: 50
<212> TYPE: DNA
<213> ORGANISM: Artificial Sequence
<220> FEATURE:
<223> OTHER INFORMATION: aptamer

<400> SEQUENCE: 10
taacgccgcc tattgtgaac gacgtgaata gtgtttgtgg gtccggagtt               50

<210> SEQ ID NO 11
<211> LENGTH: 63
<212> TYPE: DNA
<213> ORGANISM: Artificial Sequence
<220> FEATURE:
<223> OTHER INFORMATION: aptamer

<400> SEQUENCE: 11 ggataccttta acgccgccta ttgctatgag tagtgtttgt aggtctggca tgcgagttgc    60
acc                                                                   63

<210> SEQ ID NO 12
```

<211> LENGTH: 49
<212> TYPE: DNA
<213> ORGANISM: Artificial Sequence
<220> FEATURE:
<223> OTHER INFORMATION: aptamer

<400> SEQUENCE: 12
ggatacctta acgccgccta ttgctatgag tagtgtttgt aggtctggc            49

<210> SEQ ID NO 13
<211> LENGTH: 46
<212> TYPE: DNA
<213> ORGANISM: Artificial Sequence
<220> FEATURE:
<223> OTHER INFORMATION: aptamer

<400> SEQUENCE: 13
taccttaacg ccgcctattg ctatgagtag tgtttgtagg tctggc               46

<210> SEQ ID NO 14
<211> LENGTH: 41
<212> TYPE: DNA
<213> ORGANISM: Artificial Sequence
<220> FEATURE:
<223> OTHER INFORMATION: aptamer

<400> SEQUENCE: 14
taacgccgcc tattgctatg agtagtgttt gtaggtctgg c                    41

<210> SEQ ID NO 15
<211> LENGTH: 63
<212> TYPE: DNA
<213> ORGANISM: Artificial Sequence
<220> FEATURE:
<223> OTHER INFORMATION: aptamer

<400> SEQUENCE: 15
ggatacctta acgccgccta ttgcgaggtg tggctagtcg ttataggtcc accgagttgc    60
acc                                                                 63

<210> SEQ ID NO 16
<211> LENGTH: 60
<212> TYPE: DNA
<213> ORGANISM: Artificial Sequence
<220> FEATURE:
<223> OTHER INFORMATION: aptamer

<400> SEQUENCE: 16
taccttaacg ccgcctattg cgaggtgtgg ctagtcgtta taggtccacc gagttgcacc    60

<210> SEQ ID NO 17
<211> LENGTH: 55
<212> TYPE: DNA
<213> ORGANISM: Artificial Sequence
<220> FEATURE:
<223> OTHER INFORMATION: aptamer

<400> SEQUENCE: 17
taacgccgcc tattgcgagg tgtggctagt cgttataggt ccaccgagtt gcacc         55

<210> SEQ ID NO 18
<211> LENGTH: 77
<212> TYPE: DNA
<213> ORGANISM: Artificial Sequence
<220> FEATURE:
<223> OTHER INFORMATION: aptamer

<400> SEQUENCE: 18
ggttacgccc aggacacatt tcaaaagatg atggcatacg taaagggtcg aggtaagctc    60
ggtctcctcg gataatc                                                  77

<210> SEQ ID NO 19
<211> LENGTH: 77
<212> TYPE: DNA
<213> ORGANISM: Artificial Sequence
<220> FEATURE:
<223> OTHER INFORMATION: aptamer

<400> SEQUENCE: 19
ggttacgccc aggacacatt tcattgatgg catactaagg gtcgaggaat tcgtaagctc    60
ggtctcctcg gataatc                                                  77

<210> SEQ ID NO 20
<211> LENGTH: 77
<212> TYPE: DNA
<213> ORGANISM: Artificial Sequence
<220> FEATURE:
<223> OTHER INFORMATION: aptamer

<400> SEQUENCE: 20
ggttacgccc aggacacatt tcagagcgta acagtcctg gttggcaaat gtgtaagctc    60
ggtctcctcg gataatc                                                  77

<210> SEQ ID NO 21
<211> LENGTH: 77
<212> TYPE: DNA
<213> ORGANISM: Artificial Sequence
<220> FEATURE:
<223> OTHER INFORMATION: aptamer

<400> SEQUENCE: 21
ggttacgccc aggacacatt tctgtagtga agtcctggtt ggcaaattca tggtaagctc    60
ggtctcctcg gataatc                                                  77

<210> SEQ ID NO 22
<211> LENGTH: 36
<212> TYPE: DNA
<213> ORGANISM: Artificial Sequence
<220> FEATURE:
<223> OTHER INFORMATION: aptamer

<400> SEQUENCE: 22
gtgaacgacg tgaatagtgt ttgtgggtcc ggagtt                              36

<210> SEQ ID NO 23
<211> LENGTH: 75
<212> TYPE: DNA
<213> ORGANISM: Artificial Sequence
<220> FEATURE:
<223> OTHER INFORMATION: polynucleotide
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (24)..(53)
<223> OTHER INFORMATION: n is a, c, g, or t

<400> SEQUENCE: 23
ggataccttc acgccgccta ttgnnnnnnn nnnnnnnnnn nnnnnnnnnn nnngagttgc    60

```
acccgtctcg aaatc                                                      75

<210> SEQ ID NO 24
<211> LENGTH: 77
<212> TYPE: DNA
<213> ORGANISM: Artificial Sequence
<220> FEATURE:
<223> OTHER INFORMATION: polynucleotide
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (23)..(52)
<223> OTHER INFORMATION: n is a, c, g, or t

<400> SEQUENCE: 24
ggttacgccc aggacacatt tcnnnnnnnn nnnnnnnnnn nnnnnnnnnn nngtaagctc    60
ggtctcctcg gataatc                                                    77

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
ggataccttt acgccgccta ttg                                             23
```